US010662229B2

(12) United States Patent
Alewood et al.

(10) Patent No.: US 10,662,229 B2
(45) Date of Patent: May 26, 2020

(54) SPIDER VENOM PEPTIDES AND METHODS OF USE FOR MODULATING SODIUM CHANNELS

(71) Applicant: THE UNIVERSITY OF QUEENSLAND, St. Lucia, Queensland (AU)

(72) Inventors: Paul Alewood, Pullenvale (AU); Zoltan Dekan, Toowong (AU); Jennifer Deuis, Burpengary (AU); Richard Lewis, Parrearra (AU); Irina Vetter, Moorooka (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 16/312,020

(22) PCT Filed: Jun. 21, 2017

(86) PCT No.: PCT/AU2017/050629
§ 371 (c)(1),
(2) Date: Dec. 20, 2018

(87) PCT Pub. No.: WO2017/219081
PCT Pub. Date: Dec. 28, 2017

(65) Prior Publication Data
US 2019/0359662 A1 Nov. 28, 2019

(30) Foreign Application Priority Data

Jun. 21, 2016 (AU) ................................ 2016902413

(51) Int. Cl.
*A61K 38/00* (2006.01)
*C07K 14/435* (2006.01)
(52) U.S. Cl.
CPC ........ *C07K 14/43518* (2013.01); *A61K 38/00* (2013.01)
(58) Field of Classification Search
None
See application file for complete search history.

(56) References Cited

FOREIGN PATENT DOCUMENTS

WO    WO 2015/036734 A1    3/2015

OTHER PUBLICATIONS

Kimura et al. International Journal of Peptides, vol. 2012, Article ID 731293, 10 pages, doi:10.1155/2012/731293.*
International Search Report for PCT/AU2017/050629, dated Aug. 10, 2017, 5 pages.
Written Opinion of the ISA for PCT/AU2017/050629, dated Aug. 10, 2017, 5 Pages.
Klint et al., "Seven novel modulators of the analgesic target Na V 1.7 uncovered using a high-throughput venom-based discovery approach : Venom-derived inhibitors of Na V 1.7 channels", British Journal of Pharmacology, 2015, vol. 172, pp. 2445-2458.
Cardoso et al., "Identification and Characterization of ProTx-III [-TRTX-Tp1a], a New Voltage-Gated Sodium Channel Inhibitor from Venom of the Tarantula Thrixopelma pruriens", Molecular Pharmacology, 2015, vol. 88, pp. 291-303.
Chow et al., "Three Peptide Modulators of the Human Voltage-Gated Sodium Channel 1.7, an Important Analgesic Target, from the Venom of an Australian Tarantula", Toxins, 2015, vol. 7, 2494-2513.
Deuis et al., "Pharmacological characterisation of the highly NaV1.7 selective spider venom peptide Pn3a", Scientific eports, 2017, vol. 7:40883, pp. 1-18.
International Preliminary Report on Patentability, for PCT/AU2017/050629, dated Dec. 25, 2018, 7 pages.
Deuis et al., Toxins 8(3). pii: E78 (2016).
Habib et al., Pain Control, Handbook of Experimental Pharmacology, 227: 39-56 (H.-G. Schaible (ed.)) (2015).
Saez et al., Toxins 2; 2851-2871 (2010).
Clare et al., Drug Discov Today vol. 5, No. 11: 505-520 (2000).
Cox et al., Nature 444914): 894-898 (2006).
Catterall et al., Pharmacol Rev 57:397-409 (2005).
Kaczorowski et al., Frontiers in Pharmacology, vol. 2, Article 78, pp. 1-11 (2011).
Felix et al., Assay and Drug Development Technologies 2(3): 260-268 (2004).
Murray, et al., Journal of Medicinal Chemistry vol. 58, pp. 2299-2314, 2015.
Escoubas, P., et al., "Structure and Pharmacology of Spider Venom Neurotoxins," Biochimie 82 (2000) 893-907.

* cited by examiner

*Primary Examiner* — Jeanette M Lieb
(74) *Attorney, Agent, or Firm* — Nixon & Vanderhye, P.C.

(57) ABSTRACT

This invention relates to peptides and their use for modulating sodium channels. More particularly, the present invention relates to peptides from the venom of the tarantula *Pamphobeteus nigricolor* and their use in methods of inhibiting $Na_v1.7$ and for treating or preventing conditions associated with $Na_v1.7$ activity such as neuropathic, inflammatory and nociceptive pain.

20 Claims, 11 Drawing Sheets
Specification includes a Sequence Listing.

SEQUENCE LISTING

```
<160> NUMBER OF SEQ ID NOS: 24

<210> SEQ ID NO 1
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is selected from aromatic amino acid
      residues including Phe, Tyr and Trp, and small amino acid residues
      including Ser, Thr, Ala and Gly
<220> FEATURE:
<221> NAME/KEY: MISC_FEATURE
<222> LOCATION: (4)..(4)
<223> OTHER INFORMATION: Xaa is selected from hydrophobic amino acid
      residues including Met, Nle, Ile, Leu and Val
<220> FEATURE:
<221> NAME/KEY: MISC_FEATURE
<222> LOCATION: (7)..(7)
<223> OTHER INFORMATION: Xaa is selected from charged amino acid
      residues including Glu, Asp, Lys and Arg, small amino acid
      residues including Ser, Thr, Ala and Gly, and large, polar amino
      acid residues including Asn and Gln
<220> FEATURE:
<221> NAME/KEY: MISC_FEATURE
<222> LOCATION: (9)..(9)
<223> OTHER INFORMATION: Xaa is selected from charged amino acid
      residues including Glu, Asp, Lys and Arg
<220> FEATURE:
<221> NAME/KEY: MISC_FEATURE
<222> LOCATION: (12)..(12)
<223> OTHER INFORMATION: Xaa is selected from charged amino acid
      residues including Glu, Asp, Lys and Arg, and small amino acid
      residues including Ser, Thr, Ala and Gly
<220> FEATURE:
<221> NAME/KEY: MISC_FEATURE
<222> LOCATION: (22)..(22)
<223> OTHER INFORMATION: Xaa is selected from basic amino acid residues
``` including Arg and Lys
<220> FEATURE:
<221> NAME/KEY: MISC_FEATURE
<222> LOCATION: (23)..(23)
<223> OTHER INFORMATION: Xaa is selected from basic amino acid residues
      including Arg and Lys
<220> FEATURE:
<221> NAME/KEY: MISC_FEATURE
<222> LOCATION: (24)..(24)
<223> OTHER INFORMATION: Xaa is selected from hydrophobic amino acid
      residues including Met, Nle, Ile, Leu and Val

<400> SEQUENCE: 1

Cys Arg Xaa Xaa Phe Gly Xaa Cys Xaa Lys Asp Xaa Asp Cys Cys Lys
1               5                   10                  15

His Leu Gly Cys Lys Xaa Xaa Xaa Lys Tyr Cys
            20                  25

<210> SEQ ID NO 2
<211> LENGTH: 36
<212> TYPE: PRT
<213> ORGANISM: Artificial Sequence
<220> FEATURE:
<223> OTHER INFORMATION: Artificial
<220> FEATURE:
<221> NAME/KEY: MISC_FEATURE
<222> LOCATION: (1)..(1)
<223> OTHER INFORMATION: Xaa is absent or is selected from any amino
      acid residue
<220> FEATURE:
<221> NAME/KEY: MISC_FEATURE
<222> LOCATION: (2)..(2)
<223> OTHER INFORMATION: Xaa is absent or is selected from any amino
      acid residue
<220> FEATURE:
<221> NAME/KEY: MISC_FEATURE
<222> LOCATION: (5)..(5)
<223> OTHER INFORMATION: Xaa is selected from aromatic amino acid
      residues including Phe, Tyr and Trp, and small amino acid residues
      including Ser, Thr, Ala and Gly
<220> FEATURE:
<221> NAME/KEY: MISC_FEATURE
<222> LOCATION: (6)..(6)
<223> OTHER INFORMATION: Xaa is selected from hydrophobic amino acid
      residues including Met, Nle, Ile, Leu and Val
<220> FEATURE:
<221> NAME/KEY: MISC_FEATURE
<222> LOCATION: (9)..(9)
<223> OTHER INFORMATION: Xaa is selected from charged amino acid
      residues including Glu, Asp, Lys and Arg, small amino acid
      residues including Ser, Thr, Ala and Gly, and large, polar amino
      acid residues including Asn and Gln
<220> FEATURE:
<221> NAME/KEY: MISC_FEATURE
<222> LOCATION: (11)..(11)
<223> OTHER INFORMATION: Xaa is selected from charged amino acid
      residues including Glu, Asp, Lys and Arg
<220> FEATURE:
<221> NAME/KEY: MISC_FEATURE
<222> LOCATION: (14)..(14)
<223> OTHER INFORMATION: Xaa is selected from charged amino acid
      residues including Glu, Asp, Lys and Arg, and small amino acid
      residues including Ser, Thr, Ala and Gly
<220> FEATURE:
<221> NAME/KEY: MISC_FEATURE
<222> LOCATION: (24)..(24)
<223> OTHER INFORMATION: Xaa is selected from basic amino acid residues
      including Arg and Lys
<220> FEATURE:
<221> NAME/KEY: MISC_FEATURE
<222> LOCATION: (25)..(25)
<223> OTHER INFORMATION: Xaa is selected from basic amino acid residues
      including Arg and Lys
<220> FEATURE:
<221> NAME/KEY: MISC_FEATURE
<222> LOCATION: (26)..(26)

```
<223> OTHER INFORMATION: Xaa is selected from hydrophobic amino acid
      residues including Met, Nle, Ile, Leu and Val
<220> FEATURE:
<221> NAME/KEY: MISC_FEATURE
<222> LOCATION: (30)..(30)
<223> OTHER INFORMATION: Xaa is absent or is selected from any amino
      acid residue
<220> FEATURE:
<221> NAME/KEY: MISC_FEATURE
<222> LOCATION: (31)..(31)
<223> OTHER INFORMATION: Xaa is absent or is selected from any amino
      acid residue
<220> FEATURE:
<221> NAME/KEY: MISC_FEATURE
<222> LOCATION: (32)..(32)
<223> OTHER INFORMATION: Xaa is absent or is selected from any amino
      acid residue
<220> FEATURE:
<221> NAME/KEY: MISC_FEATURE
<222> LOCATION: (33)..(33)
<223> OTHER INFORMATION: Xaa is absent or is selected from any amino
      acid residue
<220> FEATURE:
<221> NAME/KEY: MISC_FEATURE
<222> LOCATION: (34)..(34)
<223> OTHER INFORMATION: Xaa is absent or is selected from any amino
      acid residue
<220> FEATURE:
<221> NAME/KEY: MISC_FEATURE
<222> LOCATION: (35)..(35)
<223> OTHER INFORMATION: Xaa is absent or is selected from any amino
      acid residue
<220> FEATURE:
<221> NAME/KEY: MISC_FEATURE
<222> LOCATION: (36)..(36)
<223> OTHER INFORMATION: Xaa is absent or is selected from any amino
      acid residue

<400> SEQUENCE: 2

Xaa Xaa Cys Arg Xaa Xaa Phe Gly Xaa Cys Xaa Lys Asp Xaa Asp Cys
1               5                   10                  15

Cys Lys His Leu Gly Cys Lys Xaa Xaa Xaa Lys Tyr Cys Xaa Xaa Xaa
            20                  25                  30

Xaa Xaa Xaa Xaa
            35

<210> SEQ ID NO 3
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent or is selected from small amino
      acid residues including Ser, Thr, Ala and Gly
<220> FEATURE:
<221> NAME/KEY: MISC_FEATURE
<222> LOCATION: (2)..(2)
<223> OTHER INFORMATION: Xaa is selected from charged amino acid
      residues including Glu, Asp, Lys and Arg, and small amino acid
      residues including Ser, Thr, Ala and Gly
<220> FEATURE:
<221> NAME/KEY: MISC_FEATURE
<222> LOCATION: (5)..(5)
<223> OTHER INFORMATION: Xaa is selected from aromatic amino acid
      residues including Phe, Tyr and Trp, and small amino acid residues
      including Ser, Thr, Ala and Gly
<220> FEATURE:
<221> NAME/KEY: MISC_FEATURE
<222> LOCATION: (6)..(6)
<223> OTHER INFORMATION: Xaa is selected from hydrophobic amino acid
      residues including Met, Nle, Ile, Leu and Val
<220> FEATURE:
```

<220> FEATURE:
<221> NAME/KEY: MISC_FEATURE
<222> LOCATION: (9)..(9)
<223> OTHER INFORMATION: Xaa is selected from charged amino acid
      residues including Glu, Asp, Lys and Arg, small amino acid
      residues including Ser, Thr, Ala and Gly, and large, polar amino
      acid residues including Asn and Gln
<220> FEATURE:
<221> NAME/KEY: MISC_FEATURE
<222> LOCATION: (11)..(11)
<223> OTHER INFORMATION: Xaa is selected from charged amino acid
      residues including Glu, Asp, Lys and Arg
<220> FEATURE:
<221> NAME/KEY: MISC_FEATURE
<222> LOCATION: (14)..(14)
<223> OTHER INFORMATION: Xaa is selected from charged amino acid
      residues including Glu, Asp, Lys and Arg, and small amino acid
      residues including Ser, Thr, Ala and Gly
<220> FEATURE:
<221> NAME/KEY: MISC_FEATURE
<222> LOCATION: (24)..(24)
<223> OTHER INFORMATION: Xaa is selected from basic amino acid residues
      including Arg and Lys
<220> FEATURE:
<221> NAME/KEY: MISC_FEATURE
<222> LOCATION: (25)..(25)
<223> OTHER INFORMATION: Xaa is selected from basic amino acid residues
      including Arg and Lys
<220> FEATURE:
<221> NAME/KEY: MISC_FEATURE
<222> LOCATION: (26)..(26)
<223> OTHER INFORMATION: Xaa is selected from hydrophobic amino acid
      residues including Met, Nle, Ile, Leu and Val

<400> SEQUENCE: 3

Xaa Xaa Cys Arg Xaa Xaa Phe Gly Xaa Cys Xaa Lys Asp Xaa Asp Cys
1               5                   10                  15

Cys Lys His Leu Gly Cys Lys Xaa Xaa Xaa Lys Tyr Cys Ala Trp Asp
            20                  25                  30

Phe Thr Phe Thr
        35

<210> SEQ ID NO 4
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is selected from hydrophobic amino acid
      residues including Met, Nle, Ile, Leu and Val
<220> FEATURE:
<221> NAME/KEY: MISC_FEATURE
<222> LOCATION: (7)..(7)
<223> OTHER INFORMATION: Xaa is selected from acidic amino acid residues
      including Glu and Asp, and small amino acid residues including
      Ser, Thr, Ala and Gly
<220> FEATURE:
<221> NAME/KEY: MISC_FEATURE
<222> LOCATION: (12)..(12)
<223> OTHER INFORMATION: Xaa is selected from acidic amino acid residues
      including Glu and Asp, and small amino acid residues including
      Ser, Thr, Ala and Gly
<220> FEATURE:
<221> NAME/KEY: MISC_FEATURE
<222> LOCATION: (22)..(22)
<223> OTHER INFORMATION: Xaa is selected from basic amino acid residues
      including Arg and Lys
<220> FEATURE:
<221> NAME/KEY: MISC_FEATURE
<222> LOCATION: (24)..(24)
<223> OTHER INFORMATION: Xaa is selected from hydrophobic amino acid
      residues including Met, Nle, Ile, Leu and Val -continued

<400> SEQUENCE: 4

Cys Arg Tyr Xaa Phe Gly Xaa Cys Glu Lys Asp Xaa Asp Cys Cys Lys
1               5                   10                  15

His Leu Gly Cys Lys Xaa Lys Xaa Lys Tyr Cys
            20              25

<210> SEQ ID NO 5
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent or is selected from any amino
      acid residue
<220> FEATURE:
<221> NAME/KEY: MISC_FEATURE
<222> LOCATION: (2)..(2)
<223> OTHER INFORMATION: Xaa is absent or is selected from any amino
      acid residue
<220> FEATURE:
<221> NAME/KEY: MISC_FEATURE
<222> LOCATION: (6)..(6)
<223> OTHER INFORMATION: Xaa is selected from hydrophobic amino acid
      residues including Met, Nle, Ile, Leu and Val
<220> FEATURE:
<221> NAME/KEY: MISC_FEATURE
<222> LOCATION: (9)..(9)
<223> OTHER INFORMATION: Xaa is selected from acidic amino acid residues
      including Glu and Asp, and small amino acid residues including
      Ser, Thr, Ala and Gly
<220> FEATURE:
<221> NAME/KEY: MISC_FEATURE
<222> LOCATION: (14)..(14)
<223> OTHER INFORMATION: Xaa is selected from acidic amino acid residues
      including Glu and Asp, and small amino acid residues including
      Ser, Thr, Ala and Gly
<220> FEATURE:
<221> NAME/KEY: MISC_FEATURE
<222> LOCATION: (24)..(24)
<223> OTHER INFORMATION: Xaa is selected from basic amino acid residues
      including Arg and Lys
<220> FEATURE:
<221> NAME/KEY: MISC_FEATURE
<222> LOCATION: (26)..(26)
<223> OTHER INFORMATION: Xaa is selected from hydrophobic amino acid
      residues including Met, Nle, Ile, Leu and Val
<220> FEATURE:
<221> NAME/KEY: MISC_FEATURE
<222> LOCATION: (30)..(30)
<223> OTHER INFORMATION: Xaa is absent or is selected from any amino
      acid residue
<220> FEATURE:
<221> NAME/KEY: MISC_FEATURE
<222> LOCATION: (31)..(31)
<223> OTHER INFORMATION: Xaa is absent or is selected from any amino
      acid residue
<220> FEATURE:
<221> NAME/KEY: MISC_FEATURE
<222> LOCATION: (32)..(32)
<223> OTHER INFORMATION: Xaa is absent or is selected from any amino
      acid residue
<220> FEATURE:
<221> NAME/KEY: MISC_FEATURE
<222> LOCATION: (33)..(33)
<223> OTHER INFORMATION: Xaa is absent or is selected from any amino
      acid residue
<220> FEATURE:
<221> NAME/KEY: MISC_FEATURE
<222> LOCATION: (34)..(34)
<223> OTHER INFORMATION: Xaa is absent or is selected from any amino
      acid residue
<220> FEATURE:
<221> NAME/KEY: MISC_FEATURE
<222> LOCATION: (35)..(35)
<223> OTHER INFORMATION: Xaa is absent or is selected from any amino
      acid residue
<220> FEATURE:
<221> NAME/KEY: MISC_FEATURE
<222> LOCATION: (36)..(36)
<223> OTHER INFORMATION: Xaa is absent or is selected from any amino
      acid residue

<400> SEQUENCE: 5

Xaa Xaa Cys Arg Tyr Xaa Phe Gly Xaa Cys Glu Lys Asp Xaa Asp Cys
1               5                   10                  15

Cys Lys His Leu Gly Cys Lys Xaa Lys Xaa Lys Tyr Cys Xaa Xaa Xaa
            20                  25                  30

Xaa Xaa Xaa Xaa
        35

<210> SEQ ID NO 6
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent or is selected from small amino
      acid residues including Ser, Thr, Ala and Gly
<220> FEATURE:
<221> NAME/KEY: MISC_FEATURE
<222> LOCATION: (2)..(2)
<223> OTHER INFORMATION: Xaa is selected from acidic amino acid residues
      including Glu and Asp, and small amino acid residues including
      Ser, Thr, Ala and Gly
<220> FEATURE:
<221> NAME/KEY: MISC_FEATURE
<222> LOCATION: (6)..(6)
<223> OTHER INFORMATION: Xaa is selected from hydrophobic amino acid
      residues including Met, Nle, Ile, Leu and Val
<220> FEATURE:
<221> NAME/KEY: MISC_FEATURE
<222> LOCATION: (9)..(9)
<223> OTHER INFORMATION: Xaa is selected from acidic amino acid residues
      including Glu and Asp, and small amino acid residues including
      Ser, Thr, Ala and Gly
<220> FEATURE:
<221> NAME/KEY: MISC_FEATURE
<222> LOCATION: (14)..(14)
<223> OTHER INFORMATION: Xaa is selected from acidic amino acid residues
      including Glu and Asp, and small amino acid residues including
      Ser, Thr, Ala and Gly
<220> FEATURE:
<221> NAME/KEY: MISC_FEATURE
<222> LOCATION: (24)..(24)
<223> OTHER INFORMATION: Xaa is selected from basic amino acid residues
      including Arg and Lys
<220> FEATURE:
<221> NAME/KEY: MISC_FEATURE
<222> LOCATION: (26)..(26)
<223> OTHER INFORMATION: Xaa is selected from hydrophobic amino acid
      residues including Met, Nle, Ile, Leu and Val

<400> SEQUENCE: 6

Xaa Xaa Cys Arg Tyr Xaa Phe Gly Xaa Cys Glu Lys Asp Xaa Asp Cys
1               5                   10                  15

Cys Lys His Leu Gly Cys Lys Xaa Lys Xaa Lys Tyr Cys Ala Trp Asp
            20                  25                  30

Phe Thr Phe Thr
        35

<210> SEQ ID NO 7

```
<211> LENGTH: 35
<212> TYPE: PRT
<213> ORGANISM: Pamphobeteus nigricolor

<400> SEQUENCE: 7

Asp Cys Arg Tyr Met Phe Gly Asp Cys Glu Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35

<210> SEQ ID NO 8
<211> LENGTH: 35
<212> TYPE: PRT
<213> ORGANISM: Pamphobeteus nigricolor

<400> SEQUENCE: 8

Gly Cys Arg Tyr Met Phe Gly Asp Cys Glu Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35

<210> SEQ ID NO 9
<211> LENGTH: 36
<212> TYPE: PRT
<213> ORGANISM: Artificial Sequence
<220> FEATURE:
<223> OTHER INFORMATION: Synthetic

<400> SEQUENCE: 9

Ser Asp Cys Arg Tyr Met Phe Gly Asp Cys Glu Lys Asp Glu Asp Cys
1               5                   10                  15

Cys Lys His Leu Gly Cys Lys Arg Lys Met Lys Tyr Cys Ala Trp Asp
            20                  25                  30

Phe Thr Phe Thr
        35

<210> SEQ ID NO 10
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Nle
<220> FEATURE:
<221> NAME/KEY: MISC_FEATURE
<222> LOCATION: (25)..(25)
<223> OTHER INFORMATION: Xaa is Nle

<400> SEQUENCE: 10

Asp Cys Arg Tyr Xaa Phe Gly Asp Cys Glu Lys Asp Glu Asp Cys Cys
1               5                   10                  15

Lys His Leu Gly Cys Lys Arg Lys Xaa Lys Tyr Cys Ala Trp Asp Phe
            20                  25                  30

Thr Phe Thr
        35
```

<210> SEQ ID NO 11
<211> LENGTH: 35
<212> TYPE: PRT
<213> ORGANISM: Artificial Sequence
<220> FEATURE:
<223> OTHER INFORMATION: Synthetic

<400> SEQUENCE: 11

```
Asp Cys Arg Tyr Met Phe Gly Asp Cys Glu Lys Asp Glu Cys Cys
1               5                   10                  15

Lys His Leu Gly Cys Lys Lys Met Lys Tyr Cys Ala Trp Asp Phe
            20                  25                  30

Thr Phe Thr
        35
```

<210> SEQ ID NO 12
<211> LENGTH: 35
<212> TYPE: PRT
<213> ORGANISM: Artificial Sequence
<220> FEATURE:
<223> OTHER INFORMATION: Synthetic

<400> SEQUENCE: 12

```
Asp Cys Arg Tyr Met Phe Gly Gly Cys Glu Lys Asp Glu Cys Cys
1               5                   10                  15

Lys His Leu Gly Cys Lys Arg Lys Met Lys Tyr Cys Ala Trp Asp Phe
            20                  25                  30

Thr Phe Thr
        35
```

<210> SEQ ID NO 13
<211> LENGTH: 35
<212> TYPE: PRT
<213> ORGANISM: Artificial Sequence
<220> FEATURE:
<223> OTHER INFORMATION: Synthetic

<400> SEQUENCE: 13

```
Asp Cys Arg Tyr Met Phe Gly Asp Cys Glu Lys Asp Ala Asp Cys Cys
1               5                   10                  15

Lys His Leu Gly Cys Lys Arg Lys Met Lys Tyr Cys Ala Trp Asp Phe
            20                  25                  30

Thr Phe Thr
        35
```

<210> SEQ ID NO 14
<211> LENGTH: 35
<212> TYPE: PRT
<213> ORGANISM: Artificial Sequence
<220> FEATURE:
<223> OTHER INFORMATION: Synthetic

<400> SEQUENCE: 14

```
Asp Cys Arg Tyr Met Phe Gly Lys Cys Glu Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35
```

<210> SEQ ID NO 15
<211> LENGTH: 35
<212> TYPE: PRT

```
<213> ORGANISM: Artificial Sequence
<220> FEATURE:
<223> OTHER INFORMATION: Synthetic

<400> SEQUENCE: 15

Asp Cys Arg Tyr Met Phe Gly Asn Cys Glu Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35

<210> SEQ ID NO 16
<211> LENGTH: 35
<212> TYPE: PRT
<213> ORGANISM: Artificial Sequence
<220> FEATURE:
<223> OTHER INFORMATION: Synthetic

<400> SEQUENCE: 16

Lys Cys Arg Tyr Met Phe Gly Asp Cys Glu Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35

<210> SEQ ID NO 17
<211> LENGTH: 35
<212> TYPE: PRT
<213> ORGANISM: Artificial Sequence
<220> FEATURE:
<223> OTHER INFORMATION: Synthetic

<400> SEQUENCE: 17

Asp Cys Arg Tyr Met Phe Gly Asp Cys Glu Lys Asp Glu Asp Cys Cys
1               5                   10                  15

Lys His Leu Gly Cys Lys Arg Arg Met Lys Tyr Cys Ala Trp Asp Phe
            20                  25                  30

Thr Phe Thr
        35

<210> SEQ ID NO 18
<211> LENGTH: 35
<212> TYPE: PRT
<213> ORGANISM: Artificial Sequence
<220> FEATURE:
<223> OTHER INFORMATION: Synthetic

<400> SEQUENCE: 18

Asp Cys Arg Ala Met Phe Gly Asp Cys Glu Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35

<210> SEQ ID NO 19
<211> LENGTH: 35
<212> TYPE: PRT
<213> ORGANISM: Artificial Sequence
<220> FEATURE:
<223> OTHER INFORMATION: Synthetic
```

<400> SEQUENCE: 19

Asp Cys Arg Tyr Met Phe Gly Asp Cys Lys Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35

<210> SEQ ID NO 20
<211> LENGTH: 35
<212> TYPE: PRT
<213> ORGANISM: Artificial Sequence
<220> FEATURE:
<223> OTHER INFORMATION: Synthetic

<400> SEQUENCE: 20

Asp Cys Arg Tyr Met Phe Gly Asp Cys Glu Lys Asp Lys Asp Cys Cys
1               5                   10                  15

Lys His Leu Gly Cys Lys Arg Lys Met Lys Tyr Cys Ala Trp Asp Phe
            20                  25                  30

Thr Phe Thr
        35

<210> SEQ ID NO 21
<211> LENGTH: 35
<212> TYPE: PRT
<213> ORGANISM: Artificial Sequence
<220> FEATURE:
<223> OTHER INFORMATION: Synthetic

<400> SEQUENCE: 21

Asp Cys Arg Tyr Met Phe Gly Asp Cys Glu Lys Asp Glu Asp Cys Cys
1               5                   10                  15

Lys His Leu Gly Cys Lys Arg Asp Met Lys Tyr Cys Ala Trp Asp Phe
            20                  25                  30

Thr Phe Thr
        35

<210> SEQ ID NO 22
<211> LENGTH: 35
<212> TYPE: PRT
<213> ORGANISM: Artificial Sequence
<220> FEATURE:
<223> OTHER INFORMATION: Synthetic

<400> SEQUENCE: 22

Asp Cys Arg Tyr Met Phe Gly Asp Cys Glu Lys Asp Glu Asp Cys Cys
1               5                   10                  15

Lys His Leu Gly Cys Lys Arg Lys Met Lys Tyr Cys Ala Ala Asp Phe
            20                  25                  30

Thr Phe Thr
        35

<210> SEQ ID NO 23
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)

```
<223> OTHER INFORMATION: ACETYLATION

<400> SEQUENCE: 23

Asp Cys Arg Tyr Met Phe Gly Asp Cys Glu Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35

<210> SEQ ID NO 24
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (35)..(35)
<223> OTHER INFORMATION: AMIDATION

<400> SEQUENCE: 24

Asp Cys Arg Tyr Met Phe Gly Asp Cys Glu Lys Asp Glu Asp Cys Cys
1               5                   10                  15

Lys His Leu Gly Cys Lys Arg Lys Met Lys Tyr Cys Ala Trp Asp Phe
            20                  25                  30

Thr Phe Thr
        35
```

SPIDER VENOM PEPTIDES AND METHODS OF USE FOR MODULATING SODIUM CHANNELS

This application is the U.S. national phase of International Application No. PCT/AU2017/050629 filed Jun. 21, 2017, which designated the U.S. and claims priority to AU Patent Application No. 2016902413 filed Jun. 21, 2016, the entire contents of each of which are hereby incorporated by reference.

FIELD OF THE INVENTION

This invention relates to peptides and their use for modulating sodium channels. More particularly, the present invention relates to peptides and their use in methods of inhibiting $Na_v1.7$ and for treating or preventing conditions associated with $Na_v1.7$ activity.

REFERENCE TO SEQUENCE LISTING SUBMITTED ELECTRONICALLY

The content of the electronically submitted sequence listing (Name: 0659_0207_Sequence_Listing_ST25.txt; Size: 19,861 bytes; and Date of Creation: Aug. 20, 2019) is herein incorporated by reference in its entirety.

BACKGROUND OF THE INVENTION

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

Venomous animals produce venom rich in bioactive components that have evolved to specifically and potently modulate a wide range of ion channels and receptors. Due to these exquisite properties, venom components have found use in the treatment and management of several conditions. For example, the analgesic drug Prialt is a peptide from the venom of the marine cone snail *Conus magus*.

Spider venoms are predominantly comprised of peptides, with some venoms containing greater than 1000 novel peptides. These venoms contain a significant number of peptides that modulate the activity of neuronal ion channels and receptors, such as voltage-gated potassium ($K_v$), calcium ($Ca_v$) and sodium ($Na_v$) channels, which is not surprising due to the paralytic function of spider venom (Saez, et al. (2010) *Toxins*, 2:2851-71).

Spider venom peptides typically adopt an inhibitor cystine knot conformation, which provides them with extraordinary chemical, thermal and biological stability. The inhibitor cystine knot comprises a ring formed by two disulfide bonds and the intervening peptide backbone, with a third disulfide bond piercing the ring, forming a pseudo-knot. The stability resulting from this conformation is advantageous for the development of peptide therapeutics.

Voltage-gated sodium channels ($Na_v$) are complex transmembrane proteins comprised of a pore-forming α-subunit and accessory β-subunits that play an essential role in the initiation and propagation of action potentials in excitable cells. $Na_v$ channels open to permit influx of sodium ions when the membrane potential is depolarized and close on repolarization. They also close on continuous depolarization by a process termed inactivation, which leaves the channel refractory (i.e. unable to open again for a period of time).

To date, apart from the related $Na_x$, which has been suggested to function as a sodium sensor (Shimizu, et al. (2007) *Neuron*, 54(1): 59-72; Hiyama, et al. (2002) *Nat Neurosci*, 5(6): 511-512), nine isoforms termed $Na_v1.1$-$Na_v1.9$ have been functionally defined as sodium-selective ion channels (Yu and Catterall (2003) *Genome Biol*, 4(3): 207). Their distinct tissue distribution as well as amenability to modulation by toxins and drugs has led to significant interest in $Na_v$ channels as therapeutic targets in a number of poorly treated conditions, ranging from epilepsy to cardiac arrhythmias and pain (Clare, et al. (2000) *Drug Discov Today*, 5(11): 506-520).

Of particular interest is $Na_v1.7$, as loss-of-function mutations in humans lead to congenital insensitivity to pain, a rare condition that results in an inability to sense pain (Ahmad, et al. (2007) *Hum. Mol. Genet.*, 16:2114-2121; Cox, et al. (2006) *Nature*, 444:894-898). Accordingly, pharmacological inhibition of $Na_v1.7$ is an exciting therapeutic strategy for the treatment of a wide range of pain types including inherited erythromelalgia and paroxysmal extreme pain disorder, two conditions whose pathophysiology arises from $Na_v1.7$ gain-of-function mutations. $Na_v1.7$ selectivity is key to developing more effective analgesics as activity at major off-targets, including the skeletal muscle isoform $Na_v1.4$, the cardiac isoform $Na_v1.5$, as well as neuronal isoforms $Na_v1.1$, $Na_v1.2$ and $Na_v1.6$, is likely to impact on the therapeutic window and cause dose-limiting adverse effects (Trimmer, et al. (1990) *Dev. Biol.*, 142:360-367; Rogart, et al. (1989) *Proc. Natl. Acad. Sci. USA*, 86:8170-8174; Caldwell, et al. (2000) *Proc. Natl. Acad. Sci. USA*, 97:5616-5620). However, achieving sufficient selectivity for $Na_v1.7$ over the other $Na_v$ isoforms is challenging due to the high sequence homology within the $Na_v$ family (Catterall, et al. (2005) *Pharmacol. Rev.*, 57:397-409).

Accordingly, there exists a need for new $Na_v$ inhibitors with greater selectivity for $Na_v1.7$ than the other $Na_v$ isoforms and which may be used for treating or preventing conditions associated with $Na_v1.7$ activity.

SUMMARY OF THE INVENTION

The present invention is predicated in part on the discovery of peptides that modulate $Na_v$ channels, particularly $Na_v1.7$. These peptides may be useful for inhibiting $Na_v1.7$ and may be useful in the treatment or prevention of conditions associated with $Na_v1.7$ activity.

In one aspect of the present invention, there is provided an isolated, synthetic or recombinant peptide comprising, consisting or consisting essentially of SEQ ID NO: 1:

[SEQ ID NO: 1]
CRXaa$_1$Xaa$_2$FGXaa$_3$CXaa$_4$KDXaa$_5$DCCKHLGCKXaa$_6$Xaa$_7$Xaa$_8$KYC wherein:
Xaa$_1$ is selected from aromatic amino acid residues including Phe, Tyr and Trp, and small amino acid residues including Ser, Thr, Ala and Gly;
Xaa$_2$ and Xaa$_8$ are independently selected from hydrophobic amino acid residues including Met, Nle, Ile, Leu and Val;
Xaa$_3$ is selected from charged amino acid residues including Glu, Asp, Lys and Arg, small amino acid residues including Ser, Thr, Ala and Gly, and large, polar amino acid residues including Asn and Gln;

Xaa$_4$ is selected from charged amino acid residues including Glu, Asp, Lys and Arg;

Xaa$_5$ is selected from charged amino acid residues including Glu, Asp, Lys and Arg, and small amino acid residues including Ser, Thr, Ala and Gly; and Xaa$_6$ and Xaa$_7$ are independently selected from basic amino acid residues including Arg and Lys.

In another aspect of the present invention, there is provided an isolated, synthetic or recombinant peptide comprising, consisting or consisting essentially of SEQ ID NO: 2:

[SEQ ID NO: 2]
Xaa$_9$Xaa$_{10}$CRXaa$_1$Xaa$_2$FGXaa$_3$CXaa$_4$KDXaa$_5$DCCKHLGCKXaa$_6$Xaa$_7$

Xaa$_8$KYCXaa$_{11}$Xaa$_{12}$Xaa$_{13}$Xaa$_{14}$Xaa$_{15}$Xaa$_{16}$Xaa$_{17}$ wherein:

Xaa$_9$, Xaa$_{10}$, Xaa$_{11}$, Xaa$_{12}$, Xaa$_{13}$, Xaa$_{14}$, Xaa$_{15}$, Xaa$_{16}$ and Xaa$_{17}$ are independently absent or are selected from any amino acid residue; and Xaa$_1$ to Xaa$_8$ are as defined for SEQ ID NO: 1.

In still another aspect of the present invention, there is provided an isolated, synthetic or recombinant peptide comprising, consisting or consisting essentially of SEQ ID NO: 3:

[SEQ ID NO: 3]
Xaa$_9$Xaa$_{10}$CRXaa$_1$Xaa$_2$FGXaa$_3$CXaa$_4$KDXaa$_5$DCCKHLGCKXaa$_6$Xaa$_7$

Xaa$_8$KYCAWDFTFT wherein:

Xaa$_9$ is absent or is selected from small amino acid residues including Ser, Thr, Ala and Gly;

Xaa$_{10}$ is selected from charged amino acid residues including Glu, Asp, Lys and Arg, and small amino acid residues including Ser, Thr, Ala and Gly; and Xaa$_1$ to Xaa$_8$ are as defined for SEQ ID NO: 1.

In a further aspect of the invention, there is provided an isolated, synthetic or recombinant peptide comprising, consisting or consisting essentially of SEQ ID NO: 4:

[SEQ ID NO: 4]
CRYXaa$_2$FGXaa$_3$CEKDXaa$_5$DCCKHLGCKXaa$_6$KXaa$_8$KYC wherein:

Xaa$_2$ and Xaa$_8$ are independently selected from hydrophobic amino acid residues including Met, Nle, Ile, Leu and Val;

Xaa$_3$ and Xaa$_5$ are independently selected from acidic amino acid residues including Glu and Asp, and small amino acid residues including Ser, Thr, Ala and Gly; and Xaa$_6$ is selected from basic amino acid residues including Arg and Lys.

In a still further aspect of the invention, there is provided an isolated, synthetic or recombinant peptide comprising, consisting or consisting essentially of SEQ ID NO: 5:

[SEQ ID NO: 5]
Xaa$_9$Xaa$_{10}$CRYXaa$_2$FGXaa$_3$CEKDXaa$_5$DCCKHLGCKXaa$_6$KXaa$_8$KYC

Xaa$_{11}$Xaa$_{12}$Xaa$_{13}$Xaa$_{14}$Xaa$_{15}$Xaa$_{16}$Xaa$_{17}$ wherein:

Xaa$_9$, Xaa$_{10}$, Xaa$_{11}$, Xaa$_{12}$, Xaa$_{13}$, Xaa$_{14}$, Xaa$_{15}$, Xaa$_{16}$ and Xaa$_{17}$ are independently absent or are selected from any amino acid residue;

Xaa$_2$ and Xaa$_8$ are independently selected from hydrophobic amino acid residues including Met, Nle, Ile, Leu and Val;

Xaa$_3$ and Xaa$_5$ are independently selected from acidic amino acid residues including Glu and Asp, and small amino acid residues including Ser, Thr, Ala and Gly; and Xaa$_6$ is selected from basic amino acid residues including Arg and Lys.

In another aspect of the invention, there is provided an isolated, synthetic or recombinant peptide comprising, consisting or consisting essentially of SEQ ID NO: 6:

[SEQ ID NO: 6]
Xaa$_9$Xaa$_{10}$CRYXaa$_2$FGXaa$_3$CEKDXaa$_5$DCCKHLGCKXaa$_6$KXaa$_8$KYC

AWDFTFT wherein:

Xaa$_9$ is absent or is selected from small amino acid residues including Ser, Thr, Ala and Gly;

Xaa$_{10}$ is selected from acidic amino acid residues including Glu and Asp, and small amino acid residues including Ser, Thr, Ala and Gly;

Xaa$_2$ and Xaa$_8$ are independently selected from hydrophobic amino acid residues including Met, Nle, Ile, Leu and Val;

Xaa$_3$ and Xaa$_5$ are independently selected from acidic amino acid residues including Glu and Asp, and small amino acid residues including Ser, Thr, Ala and Gly; and Xaa$_6$ is selected from basic amino acid residues including Arg and Lys.

In another aspect of the present invention, there is provided a composition comprising a peptide of the invention and a pharmaceutically acceptable carrier or diluent.

In yet another aspect of the present invention, there is provided a method of inhibiting Na$_v$1.7, comprising contacting a Na$_v$1.7 expressing cell with a peptide of the invention.

A further aspect of the present invention provides a method of treating or preventing a condition in respect of which inhibition of Na$_v$1.7 activity is associated with effective treatment, comprising administration of a peptide of the invention.

In a still further aspect of the present invention, there is provided a method of treating neuropathic pain, inflammatory pain, or nociceptive pain comprising administration of a peptide of the invention to a subject in need thereof.

Na$_v$1.8. (A) Pnc1a most potently inhibited Na$_v$1.7 (pIC$_{50}$ 6.67±0.09 M) with greater than 10 fold selectivity over Na$_v$1.2 (pIC$_{50}$ 5.53±0.1 M), Na$_v$1.3 (pIC$_{50}$ 5.09±0.2 M), greater than 50 fold selectivity over Na$_v$1.4 (pIC$_{50}$ 4.95±0.04 M), Na$_v$1.1 (pIC$_{50}$ 4.88±0.2 M) and Na$_v$1.6 (pIC$_{50}$ 4.73±0.2 M), and greater than 100 fold selectivity over Na$_v$1.8 (pIC$_{50}$ 4.58±0.2 M) and the major off target, Na$_v$1.5 (pIC$_{50}$ 4.07±0.1 M). Data are presented as mean±SEM from 3-6 independent experiments. (B) Representative concentration response curves of Pnc1a at hNa$_v$1.1-Na$_v$1.8.

Figure 3:
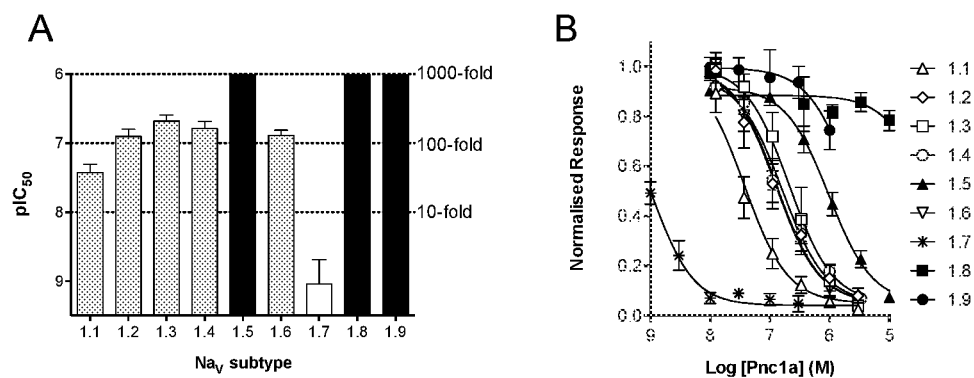

FIG. 3 Na$_v$ subtype activity of Pnc1a assessed using automated patch clamping. (A) Activity of synthetic Pnc1a assessed in HEK cells heterologously expressing Na$_v$1.1-Na$_v$1.9. Pnc1a most potently inhibited Na$_v$1.7 (pIC$_{50}$>9.04±0.4 M), with greater than 30-fold selectivity over Na$_v$1.1 (pIC$_{50}$ 7.43±0.1 M), greater than 100-fold selectivity over Na$_v$1.2 (pIC$_{50}$ 6.90±0.1 M), Na$_v$1.3 (pIC$_{50}$ 6.68±0.1 M), Na$_v$1.4 (pIC$_{50}$ 6.80±0.1 M) and Na$_v$1.6 (pIC$_{50}$ 6.89±0.1 M), and greater than 1000-fold selectivity over Na$_v$1.5 (pIC$_{50}$ 6.01±0.1 M), Na$_v$1.8 (pIC$_{50}$ 4.32±0.1 M) and Na$_v$1.9 (pIC$_{50}$ 5.63±0.1 M). Data are presented as mean±SEM for 3-9 cells per subtype. (B) Representative concentration response curves of Pnc1a at hNa$_v$1.1-Na$_v$1.9.

Figure 4:
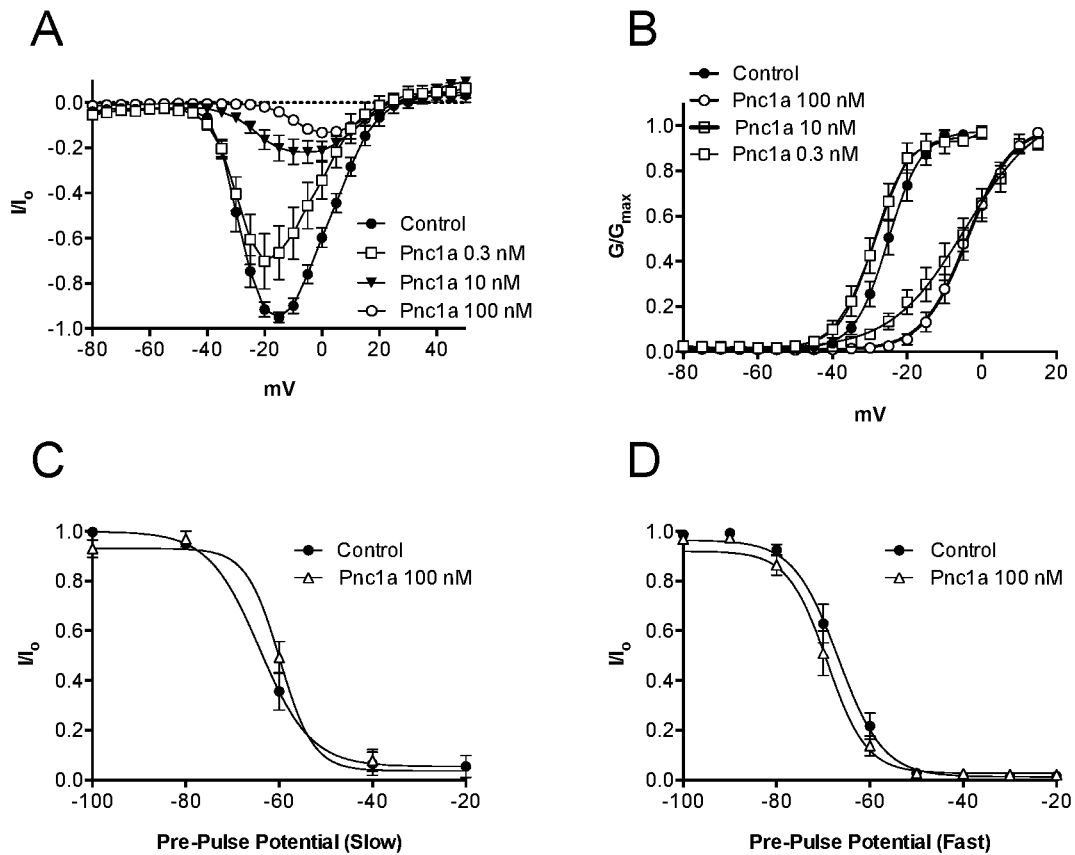

FIG. 4 Mechanism of action of Pnc1a at hNa$_v$1.7. Activity of synthetic Pnc1a in HEK cells heterologously expressing Na$_v$1.7 assessed by automated patch clamping. (A) Current-voltage (IV) relationship before and after addition of Pnc1a (0.3 nM, 10 nM, 100 nM). Currents were evoked from a holding potential of −80 mV, a prepulse to −100 mV, and 5 mV steps from −80 to 50 mV. (B) Pnc1a concentration dependently shifted the voltage dependence of activation to a more depolarised potential (V$_{50}$; Control, −25.1±0.5 mV; Pnc1a (100 nM), −3.82±0.8 mV; Pnc1a (10 nM), −4.40±2.2 mV; Pnc1a (0.3 nM), −28.94±0.66 mV). (C) Pnc1a (100 nM) had no effect on the voltage dependence of slow inactivation or (D) fast inactivation. Data are presented as mean±SEM, n=3-10.

Figure 5:
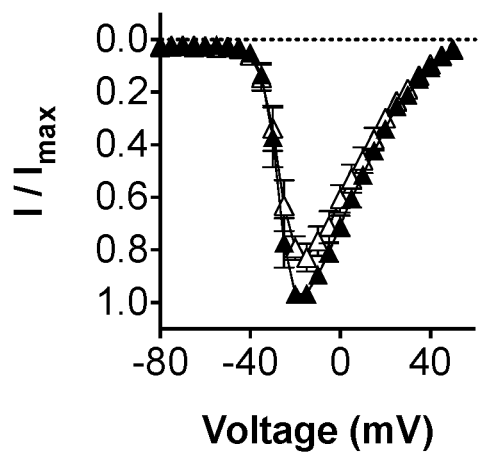

FIG. 5 Activity of [K24D]Pnc1a at hNa$_v$1.7. Current-voltage (IV) relationship before (control; ▲) and after addition of [K24D]Pnc1a (100 nM; Δ) in HEK cells heterologously expressing hNa$_v$1.7 assessed by automated patch clamping. Data is presented as mean±SEM, n=3-10.

Figure 6:
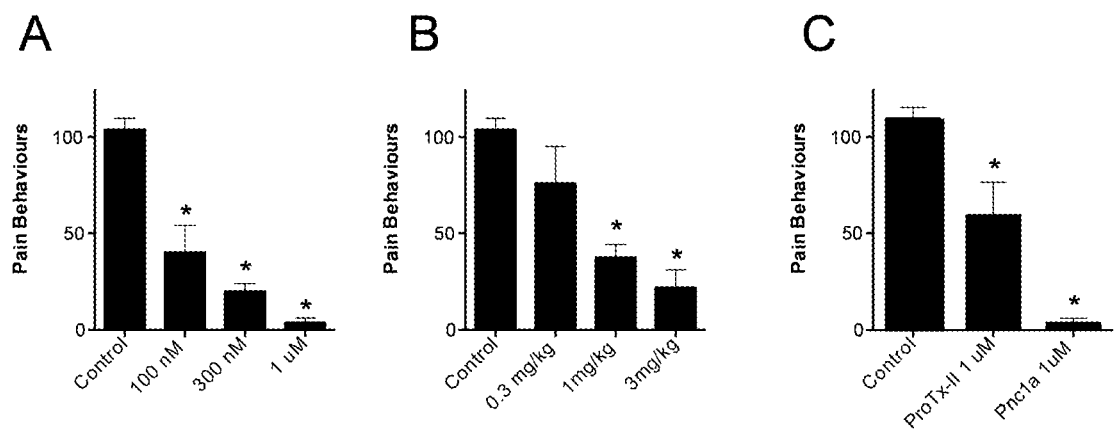

FIG. 6 Effect of Pnc1a on pain behaviours in the OD1 model. (A) Intraplantar administration of Pnc1a (100 nM, 300 nM, 1 μM) concentration-dependently reversed spontaneous pain behaviours in mice evoked by OD1. (B) Intraperitoneal administration of Pnc1a (0.3, 1, 3 mg/kg) dose-dependently reduced spontaneous pain behaviours in mice evoked by OD1. (C) Intraplantar administration of the Na$_v$1.7 selective inhibitor ProTxII (1 μM) only partially reversed OD1-induced pain behaviours compared to an equivalent concentration of Pnc1a. Data is presented as cumulative pain behaviours occurring 10 min after injection of OD1. Statistical significance was determined using One-way ANOVA with Dunnett's post test, *P<0.05 compared to vehicle control. Data are presented as mean±SEM, n=3-9 per group.

Figure 7:
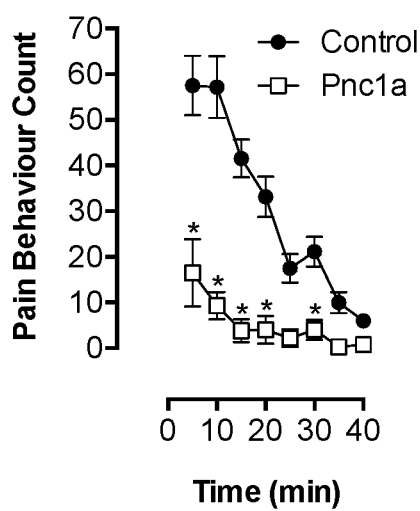

FIG. 7 Effect of intraperitoneal administration of Pnc1a (3 mg/kg) over time on OD1-induced spontaneous pain behaviours.

Figure 8:
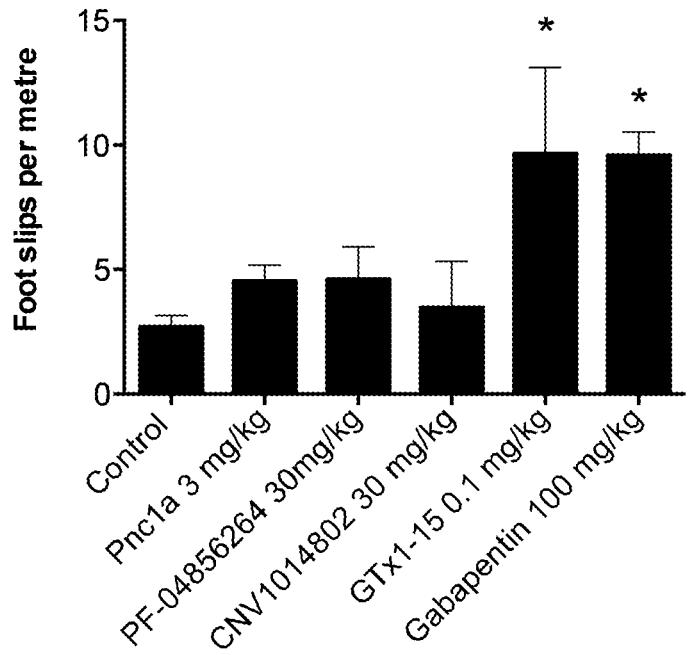

FIG. 8 Motor assessment of systemically delivered Pnc1a compared to other Na$_v$1.7 clinical candidates and the adjuvant analgesic gabapentin. Ataxia index (number of foot slips per metres travelled) assessed by the Parallel Rod Test. Pnc1a (3 mg/kg, i.p.), PF-04856254 (30 mg/kg, i.p.) and CNV1014802 (30 mg/kg, i.p.) had no significant effect compared to vehicle control while the spider peptide GpTx-1 (0.1 mg/kg, i.p.) and gabapentin (100 mg/kg, i.p.) caused a significant increase in the ataxia index. Statistical significance was determined using one-way ANOVA with Dunnett's post test, *P<0.05 compared to vehicle control. Data are presented as mean±SEM, n=3-12 per group.

Figure 9:
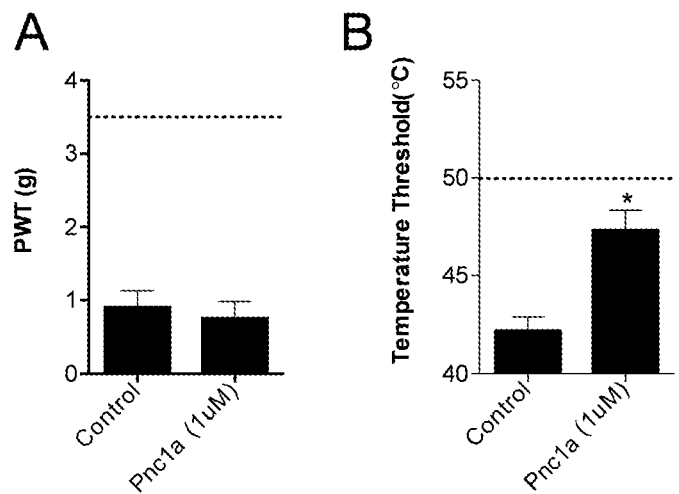

FIG. 9 Effect of Pnc1a on burns-induced pain. (A) Intraplantar administration of Pnc1a had no significant effect on the mechanical threshold, (B) but significantly increased the thermal threshold of the injured paw. Statistical significance was determined using t-test, *P<0.05 compared to vehicle control. Data are presented as mean±SEM, n=4-6 per group.

Figure 10:
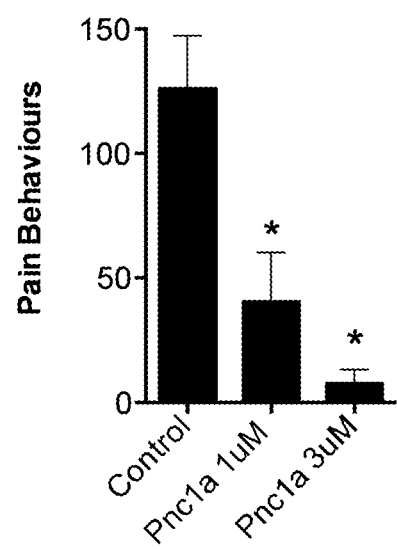

FIG. 10 Effect of Pnc1a on ciguatoxin-induced spontaneous pain. Intraplantar administration of Pnc1a significantly reduced spontaneous pain behaviours. Statistical significance was determined using t-test, *P<0.05 compared to vehicle control. Data are presented as mean±SEM, n=3-9 per group.

Figure 11:
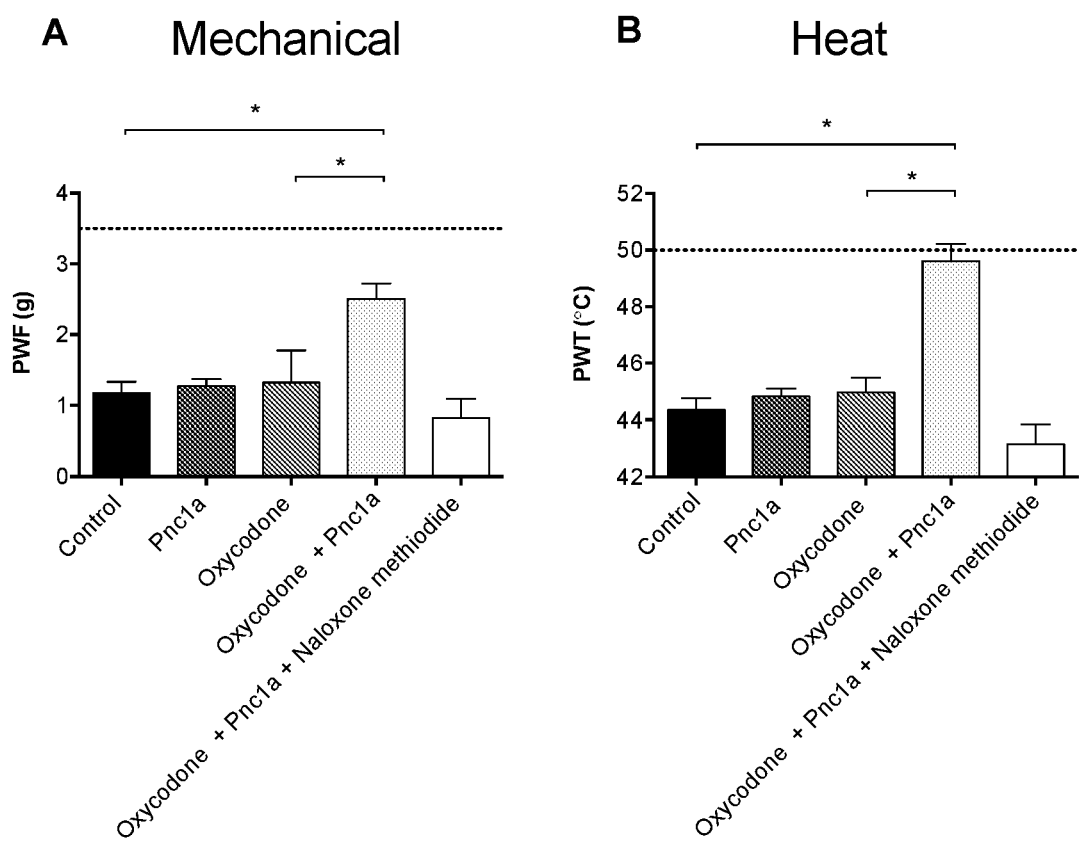

FIG. 11 Pnc1a synergizes with oxycodone to produce analgesia in the carrageenan model. (A) Effects of Pnc1a (3 mg/kg, i.p.), oxycodone (0.3 mg/kg, i.p.) and the combination of Pnc1a (3 mg/kg, i.p.) and oxycodone (0.3 mg/kg, i.p.) on mechanical thresholds. The combination of Pnc1a and oxycodone significantly alleviated mechanical allodynia compared to vehicle control and oxycodone alone. The analgesic effects of the combination were reversed by the peripherally restricted opioid antagonist naloxone methiodide (100 mg/kg, i.p.). (B) Effects of Pnc1a (3 mg/kg, i.p.), oxycodone (1 mg/kg, i.p.) and the combination of Pnc1a (3 mg/kg, i.p.) and oxycodone (1 mg/kg, i.p.) on thermal thresholds. The combination of Pnc1a and oxycodone significantly alleviated thermal allodynia compared to vehicle control and oxycodone alone. The analgesic effects of the combination were reversed by the peripherally restricted opioid antagonist naloxone methiodide (100 mg/kg, i.p.). Statistical significance was determined using t-test, *P<0.05 compared to vehicle control. Data are presented as mean±SEM, n=3-10 per group.

Figure 12:
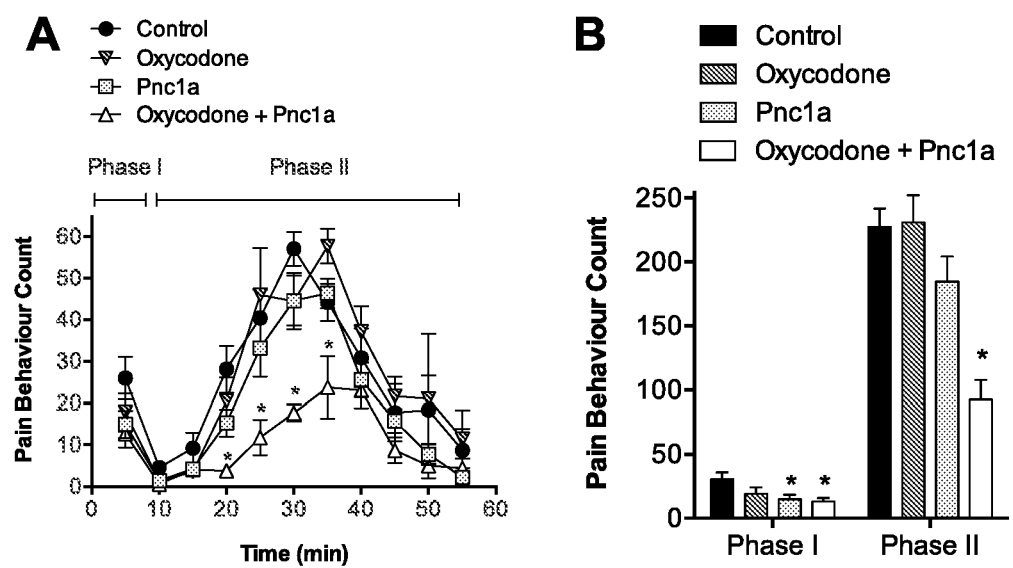

FIG. 12 Pnc1a synergizes with oxycodone to produce analgesia in the formalin model. (A) Time course of Pnc1a (3 mg/kg, i.p.), oxycodone (1 mg/kg, i.p.) and the combination of Pnc1a (3 mg/kg, i.p.) and oxycodone (1 mg/kg, i.p.) on spontaneous flinching in the formalin model. (B) The combination of Pnc1a and oxycodone significantly reduced spontanous pain behaviours compared to vehicle control in Phase I and II. Statistical significance was determined using t-test, *P<0.05 compared to vehicle control. Data are presented as mean±SEM, n=7-10 per group.

Figure 13:
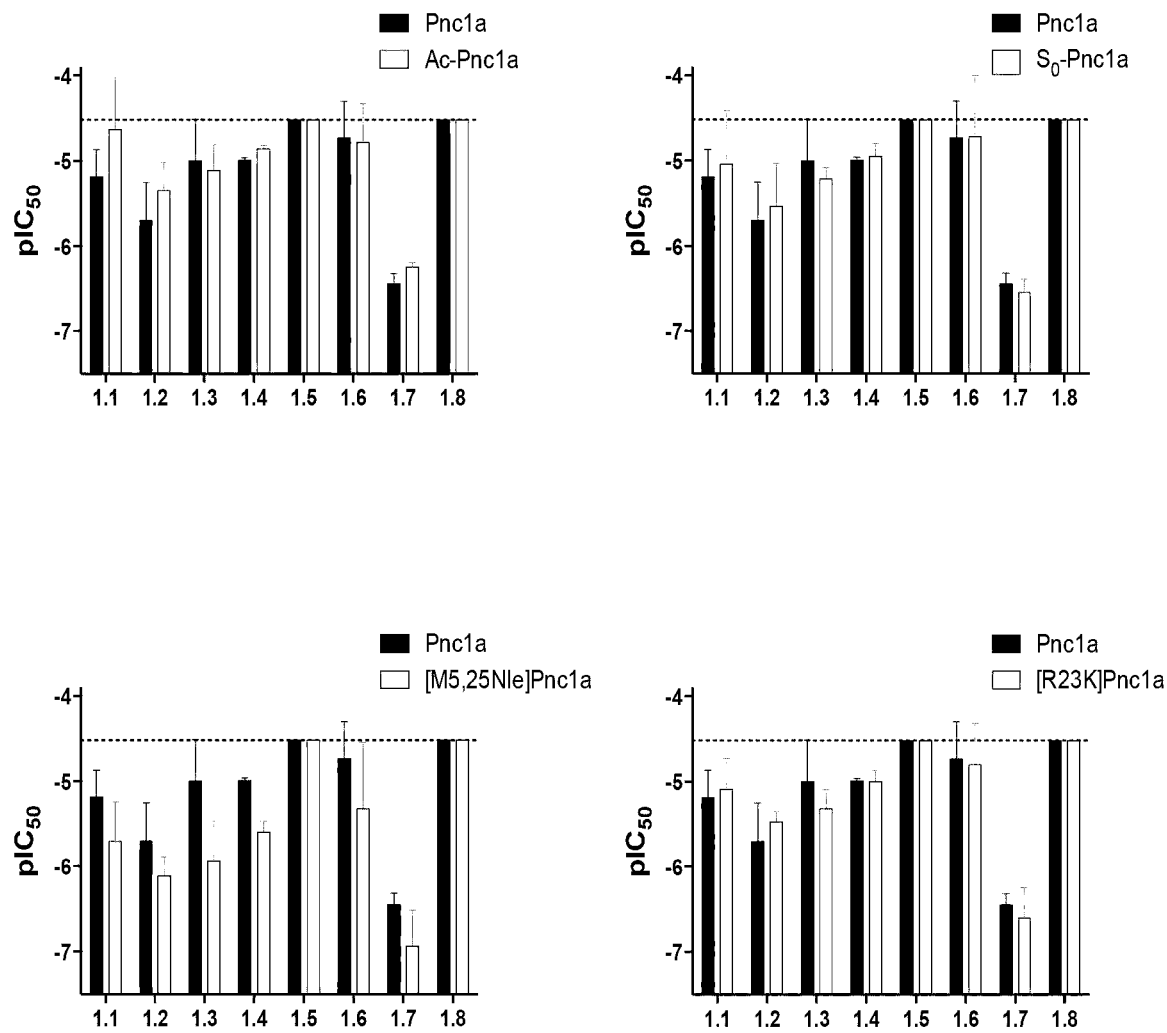
Figure 13:
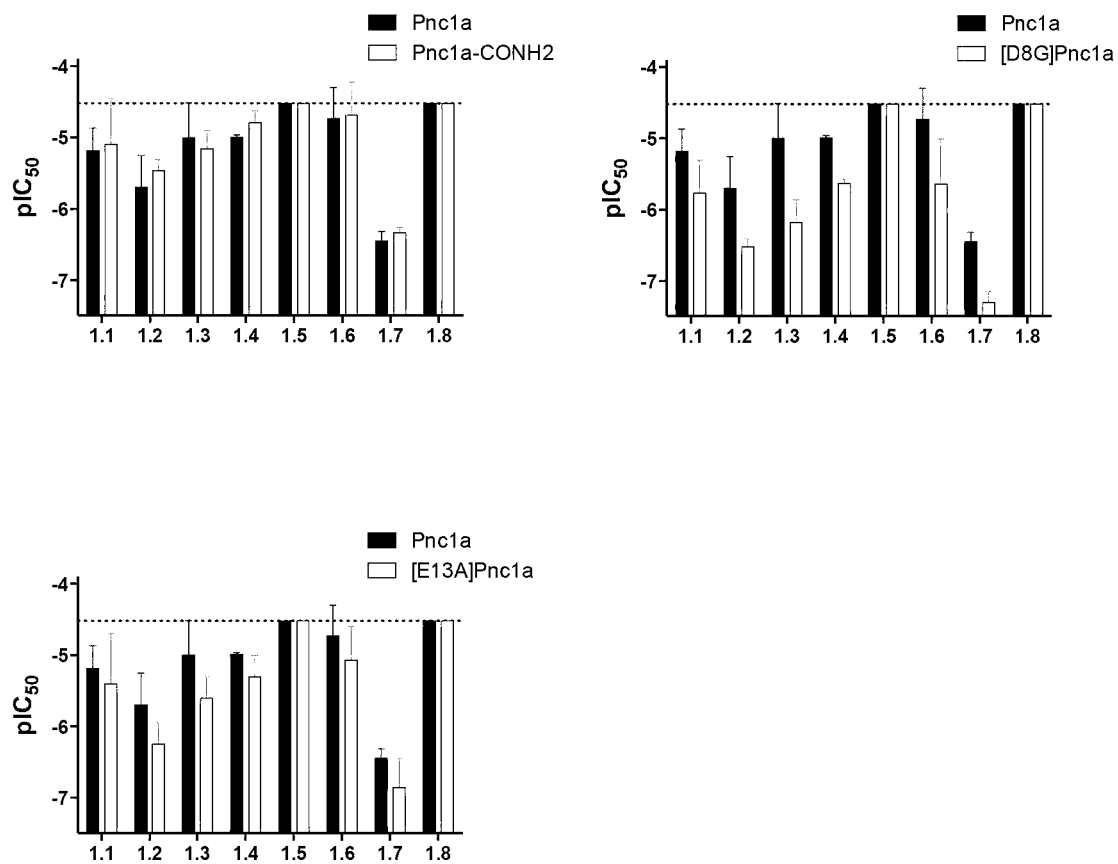

FIG. 13 Na$_v$ subtype selectivity of Pnc1a analogues assessed using membrane potential assays. Activity of synthetic Pnc1a analogues was assessed in HEK cells heterologously expressing hNa$_v$1.1-Na$_v$1.8. Data are presented as mean±SEM from 3 independent experiments.

Figure 14:
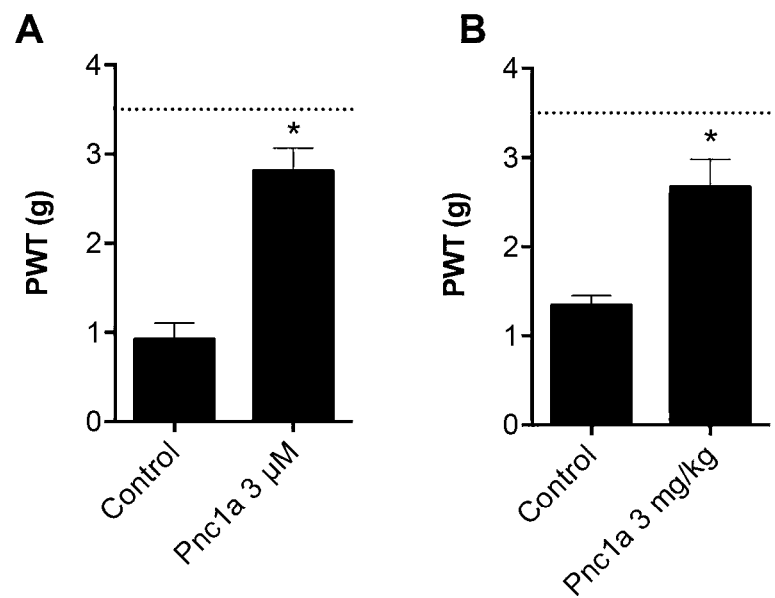

FIG. 14 Effect of Pnc1a on post-operative pain. (A) Effect of intraplantar administration of Pnc1a (3 μM) compared to vehicle control on the mechanical threshold of the injured paw. (B) Effect of intraperitoneal administration of Pnc1a (3 mg/kg) compared to vehicle control on the mechanical threshold of the injured paw. Statistical significance was determined using t-test, *P<0.05 compared to vehicle control. Data are presented as mean±SEM, n=5-6 per group.

Figure 15:
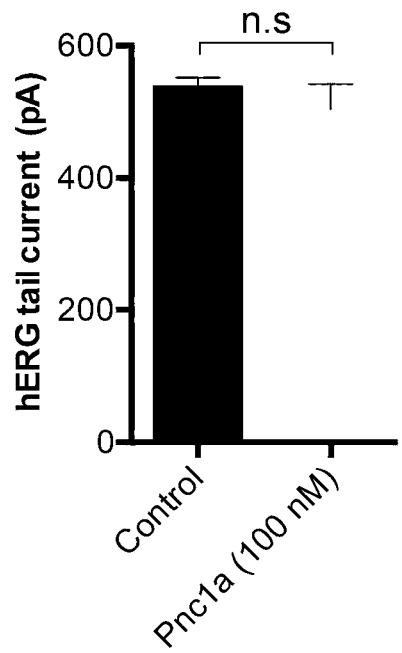

FIG. 15 Activity of Pnc1a in CHO cells heterologously expressing hERG. Statistical significance was determined using paired t-test, *P<0.05 compared to buffer control. Data are presented as mean±SEM, n=4 cells.

Figure 16:
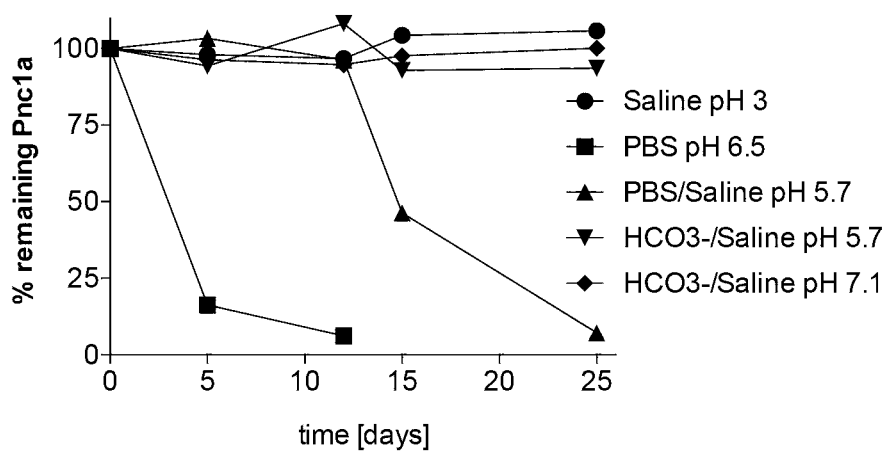

FIG. 16 Stability of Pnc1a in saline (pH 3), phosphate buffered saline (PBS; pH 6.5), PBS/saline (pH 5.7), and bicarbonate buffered saline ($HCO_3^-$/saline; pH 5.7 and pH 7.1).

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to conditions (e.g. amounts, concentrations, time, etc.) that vary by as much as 30%, especially by as much as 20%, and more especially by as much as 10%, 9%, 8%, 7%, 6%, 5%, 4%, 3%, 2% or 1% to a specified condition.

The term "agent" is used herein to refer to a compound that induces a desired pharmacological and/or physiological effect. The term "agent" is not to be construed narrowly but can be any compound, such as an inorganic or organic compound, a peptide, a nucleic acid, a carbohydrate, a lipid, an antibody, a protein or a combination thereof. The term "agent" extends to small molecules, macromolecules and cellular agents.

As used herein, the term "and/or" refers to and encompasses any and all possible combinations of one or more of the associated listed items, as well as the lack of combinations when interpreted in the alternative (or).

The terms "antagonist", "inhibitor" and "blocker" are used interchangeably herein to refer to agents that reduce, inhibit, impair or prevent ion transfer across a cell membrane.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, the use of the term "comprising" and the like indicates that the listed integers are required or mandatory, but that other integers are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. In specific embodiments, the term "consisting essentially of", in the context of a specific amino acid sequence disclosed herein, includes within its scope about 1 to about 50 optional amino acids (and all integer optional amino acids in between) upstream of the specific amino acid sequence and/or about 1 to about 50 optional amino acids (and all integer optional amino acids in between) downstream of the specific amino acid sequence.

As used herein, the term "condition" refers to an abnormality in the physical state of the body as a whole or one of its parts.

As used herein, the terms "inhibitor cystine knot" and "inhibitor cystine knot motif" refer to a structural motif wherein a ring formed by two disulfide bonds and the intervening peptide backbone is pierced by a third disulfide bond.

As used herein, the term "dosage unit form" refers to physically discrete units suited as unitary dosages for the subject to be treated, each unit containing a predetermined quantity of active material calculated to produce the desired therapeutic effect in association with the required pharmaceutically acceptable vehicle.

As used herein, the term "$Na_v1.7$ inhibitor" and grammatical variants thereof refers to an agent that reduces, inhibits, impairs or prevents the conduction of sodium ions through $Na_v1.7$. In particular embodiments, the $Na_v1.7$ inhibitor inhibits the conduction of sodium ions through $Na_v1.7$.

As used herein, the term "isolated" refers to material that is substantially or essentially free from components that normally accompany it in its native state. For example, an "isolated peptide" refers to in vitro isolation and/or purification of a peptide from its natural cellular environment and from association with other components of the cell.

As used herein, the term "$Na_v1.7$" refers to any subunit of $Na_v1.7$, unless expressly stated.

The term "$Na_v1.7$ expressing cell" is used herein to refer to a vertebrate cell, particularly a mammalian or avian cell, especially a mammalian cell, that expresses at least one $Na_v1.7$ channel. The cell may be a vertebrate cell, such as a primate cell; an avian (bird) cell; a livestock animal cell such as a sheep cell, cow cell, horse cell, deer cell, donkey cell and pig cell; a laboratory test animal cell such as a rabbit cell, mouse cell, rat cell, guinea pig cell and hamster cell; a companion animal cell such as a cat cell and dog cell; and a captive wild animal cell such as a fox cell, deer cell and dingo cell. In particular embodiments, the $Na_v1.7$ expressing cell is a human cell. In specific embodiments, the $Na_v1.7$ expressing cell is a neuronal cell, especially a sensory or sympathetic neuron, most especially a sensory neuron such as a nociceptor.

The term "operably linked" as used herein means placing a structural gene under the regulatory control of a regulatory element including, but not limited to, a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e. the genes from which it is derived.

As used herein, the terms "peptide", "protein" and "proteinaceous molecule" are used interchangeably to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject peptides are particularly useful. Included within the definition are, for example, peptides containing one or more analogues of an amino acid including, for example, unnatural amino acids or peptides with substituted linkages.

As used herein, the terms "salts" and "prodrugs" include any pharmaceutically acceptable salt, ester, hydrate or any other compound which, upon administration to the recipient, is capable of providing (directly or indirectly) a peptide of the invention, or an active metabolite or residue thereof. Suitable pharmaceutically acceptable salts include salts of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkyl ammonium. Also, basic nitrogen-containing groups may be quaternized with such agents as lower alkyl halides, such as methyl, ethyl, propyl and butyl chlorides, bromides and iodides; dialkyl sulfates such as dimethyl and diethyl sulfate; and others. However, it will be appreciated that non-pharmaceutically acceptable salts also fall within the scope of the invention since these may be useful in the preparation of pharmaceutically acceptable salts. The preparation of salts and prodrugs can be carried out by methods known in the art. For example, metal salts can be prepared by reaction of a peptide of the invention with a metal hydroxide. An acid salt can be prepared by reacting an appropriate acid with a peptide of the invention.

The terms "selective" and "selectivity" as used herein refer to agents that modulate (e.g. inhibit) an ion channel subtype of interest without displaying substantial modulation of one or more other ion channel subtypes. Accordingly, an agent that is selective for $Na_v1.7$ exhibits $Na_v1.7$ selectivity of greater than about 2-fold, 5-fold, 10-fold, 20-fold, 50-fold, 100-fold or greater than about 500-fold with respect to modulation of one or more other $Na_v$ subtypes (i.e. $Na_v1.1$-1.6, $Na_v1.8$ and $Na_v1.9$).

By "simultaneously" is meant that the active agents are administered at substantially the same time, and desirably together in the same formulation. The term "separately" as used herein means that the agents are administered at an interval, for example, at an interval of about one day to several weeks or months. The active agents may be administered in any order. The term "sequentially" as used herein means that the agents are administered in sequence, for example, at an interval of minutes, hours, days or weeks. If appropriate, the active agents may be administered in a regular repeating cycle.

As used herein, the term "solvate" refers to a complex of variable stoichiometry formed by a solute, such as a peptide of the invention, and a solvent. Such solvents should not interfere with the biological activity of the solute.

The term "stringency" as used herein, refers to the temperature and ionic strength conditions, and presence or absence of certain organic solvents during hybridization and washing procedures. The higher the stringency, the higher will be the degree of complementarity between immobilized target nucleotide sequences and the labelled probe polynucleotide sequences that remain hybridized to the target after washing. The term "high stringency" refers to temperature and ionic conditions under which only nucleotide sequences having a high frequency of complementary bases will hybridize. The stringency required is nucleotide sequence dependent and depends upon the various components present during hybridization. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

The term "subject" as used herein refers to a vertebrate subject, particularly a mammalian or avian subject, especially a mammalian subject, for whom therapy or prophylaxis is desired. Suitable subjects include, but are not limited to, primates; avians (birds); livestock animals such as sheep, cows, horses, deer, donkeys and pigs; laboratory test animals such as rabbits, mice, rats, guinea pigs and hamsters; companion animals such as cats and dogs; and captive wild animals such as foxes, deer and dingoes. In particular embodiments, the subject is a human. However, it will be understood that the aforementioned terms do not imply that symptoms are present.

Throughout the specification both single letter and three letter codes have been used to denote different amino acids. The three letter code "Nle" is used to denote norleucine throughout the specification.

2. Peptides that Inhibit $Na_v1.7$

The present invention is based, in part, on the identification of peptides that inhibit $Na_v1.7$. Thus, the inventors conceived that the peptides of the invention may be used for the treatment or prevention of conditions associated with $Na_v1.7$ activity, particularly conditions in respect of which inhibition of $Na_v1.7$ activity is associated with effective treatment.

In one aspect of the present invention, there is provided an isolated, synthetic or recombinant peptide comprising, consisting or consisting essentially of SEQ ID NO: 1:

[SEQ ID NO: 1]
CRXaa$_1$Xaa$_2$FGXaa$_3$CXaa$_4$KDXaa$_5$DCCKHLGCKXaa$_6$Xaa$_7$Xaa$_8$KYC wherein:
Xaa$_1$ is selected from aromatic amino acid residues including Phe, Tyr and Trp, and small amino acid residues including Ser, Thr, Ala and Gly;
Xaa$_2$ and Xaa$_8$ are independently selected from hydrophobic amino acid residues including Met, Nle, Ile, Leu and Val;
Xaa$_3$ is selected from charged amino acid residues including Glu, Asp, Lys and Arg, small amino acid residues including Ser, Thr, Ala and Gly, and large, polar amino acid residues including Asn and Gln;

$Xaa_4$ is selected from charged amino acid residues including Glu, Asp, Lys and Arg;

$Xaa_5$ is selected from charged amino acid residues including Glu, Asp, Lys and Arg, and small amino acid residues including Ser, Thr, Ala and Gly; and $Xaa_6$ and $Xaa_7$ are independently selected from basic amino acid residues including Arg and Lys.

In some embodiments, $Xaa_1$ to $Xaa_8$ are selected from a combination of one or more of the following:

$Xaa_1$ is Tyr or Ala;

$Xaa_2$ is Nle;

$Xaa_3$ is Asp, Gly, Lys or Asn;

$Xaa_4$ is Glu or Lys;

$Xaa_5$ is Glu, Ala or Lys;

$Xaa_6$ is Arg or Lys;

$Xaa_7$ is Arg or Lys; and $Xaa_8$ is Nle.

In another aspect of the present invention, there is provided an isolated, synthetic or recombinant peptide comprising, consisting or consisting essentially of SEQ ID NO: 2:

[SEQ ID NO: 2]
$Xaa_9Xaa_{10}CRXaa_1Xaa_2FGXaa_3CXaa_4KDXaa_5DCCKHLGCKXaa_6Xaa_7$
$Xaa_8KYCXaa_{11}Xaa_{12}Xaa_{13}Xaa_{14}Xaa_{15}Xaa_{16}Xaa_{17}$ wherein:

$Xaa_9$, $Xaa_{10}$, $Xaa_{11}$, $Xaa_{12}$, $Xaa_{13}$, $Xaa_{14}$, $Xaa_{15}$, $Xaa_{16}$ and $Xaa_{17}$ are independently absent or are selected from any amino acid residue; and $Xaa_1$ to $Xaa_8$ are as defined for SEQ ID NO: 1.

In some embodiments, $Xaa_9$ to $Xaa_{17}$ are selected from a combination of one or more of the following:

$Xaa_9$ is absent or is selected from small amino acid residues including Ser, Thr, Ala and Gly;

$Xaa_{10}$ is absent or is selected from charged amino acid residues including Glu, Asp, Lys and Arg, and small amino acid residues including Ser, Thr, Ala and Gly;

$Xaa_{11}$ is absent or is selected from small amino acid residues including Ser, Thr, Ala and Gly;

$Xaa_{12}$ is absent or is selected from aromatic amino acid residues including Phe, Tyr and Trp;

$Xaa_{13}$ is absent or is selected from acidic amino acid residues including Glu and Asp;

$Xaa_{14}$ is absent or is selected from aromatic amino acid residues including Phe, Tyr and Trp;

$Xaa_{15}$ is absent or is selected from small amino acid residues including Ser, Thr, Ala and Gly;

$Xaa_{16}$ is absent or is selected from aromatic amino acid residues including Phe, Tyr and Trp; and $Xaa_{17}$ is absent or is selected from small amino acid residues including Ser, Thr, Ala and Gly.

In some embodiments, $Xaa_9$ is absent or is Ser and/or $Xaa_{10}$ is Asp, Lys or Gly.

In some embodiments, $Xaa_{12}$ is Trp.

In some embodiments, $Xaa_{11}$ is Ala, $Xaa_{12}$ is Trp, $Xaa_{13}$ is Asp, $Xaa_{14}$ and $Xaa_{16}$ are Phe, and $Xaa_{15}$ and $Xaa_{17}$ are Thr.

In a further aspect of the present invention, there is provided an isolated, synthetic or recombinant peptide comprising, consisting or consisting essentially of SEQ ID NO: 3:

[SEQ ID NO: 3]
$Xaa_9Xaa_{10}CRXaa_1Xaa_2FGXaa_3CXaa_4KDXaa_5DCCKHLGCKXaa_6Xaa_7$
$Xaa_8KYCAWDFTFT$ wherein:

$Xaa_9$ is absent or is selected from small amino acid residues including Ser, Thr, Ala and Gly;

$Xaa_{10}$ is selected from charged amino acid residues including Glu, Asp, Lys and Arg, and small amino acid residues including Ser, Thr, Ala and Gly; and $Xaa_1$ to $Xaa_8$ are as defined for SEQ ID NO: 1.

In some embodiments, $Xaa_9$ is absent or is Ser, and/or $Xaa_{10}$ is Asp, Gly or Lys.

In a still further aspect of the invention, there is provided an isolated, synthetic or recombinant peptide comprising, consisting or consisting essentially of SEQ ID NO: 4:

[SEQ ID NO: 4]
$CRYXaa_2FGXaa_3CEKDXaa_5DCCKHLGCKXaa_6KXaa_8KYC$ wherein:

$Xaa_2$ and $Xaa_8$ are independently selected from hydrophobic amino acid residues including Met, Nle, Ile, Leu and Val;

$Xaa_3$ and $Xaa_5$ are independently selected from acidic amino acid residues including Glu and Asp, and small amino acid residues including Ser, Thr, Ala and Gly; and $Xaa_6$ is selected from basic amino acid residues including Arg and Lys.

In some embodiments, $Xaa_2$, $Xaa_3$, $Xaa_5$, $Xaa_6$ and $Xaa_8$ are selected from a combination of one or more of the following:

$Xaa_2$ is Nle;

$Xaa_3$ is Asp or Gly;

$Xaa_5$ is Glu or Ala;

$Xaa_6$ is Arg or Lys; and $Xaa_8$ is Nle.

In another aspect of the invention, there is provided an isolated, synthetic or recombinant peptide comprising, consisting or consisting essentially of SEQ ID NO: 5:

[SEQ ID NO: 5]
$Xaa_9Xaa_{10}CRYXaa_2FGXaa_3CEKDXaa_5DCCKHLGCKXaa_6KXaa_8KYC$
$Xaa_{11}Xaa_{12}Xaa_{13}Xaa_{14}Xaa_{15}Xaa_{16}Xaa_{17}$ wherein:

$Xaa_9$, $Xaa_{10}$, $Xaa_{11}$, $Xaa_{12}$, $Xaa_{13}$, $Xaa_{14}$, $Xaa_{15}$, $Xaa_{16}$ and $Xaa_{17}$ are independently absent or are selected from any amino acid residue;

$Xaa_2$ and $Xaa_8$ are independently selected from hydrophobic amino acid residues including Met, Nle, Ile, Leu and Val;

$Xaa_3$ and $Xaa_5$ are independently selected from acidic amino acid residues including Glu and Asp, and small amino acid residues including Ser, Thr, Ala and Gly; and $Xaa_6$ is selected from basic amino acid residues including Arg and Lys.

In some embodiments, $Xaa_2$, $Xaa_3$, $Xaa_5$, $Xaa_6$ and $Xaa_8$ are selected from a combination of one or more of the following:

$Xaa_2$ is Nle;

$Xaa_3$ is Asp or Gly;

$Xaa_5$ is Glu or Ala;

$Xaa_6$ is Arg or Lys; and $Xaa_8$ is Nle.

In some embodiments, $Xaa_9$ to $Xaa_{17}$ are selected from a combination of one or more of the following:

Xaa$_9$ is absent or is selected from small amino acid residues including Ser, Thr, Ala and Gly;
Xaa$_{10}$ is absent or is selected from acidic amino acid residues including Glu and Asp, and small amino acid residues including Ser, Thr, Ala and Gly;
Xaa$_{11}$ is absent or is selected from small amino acid residues including Ser, Thr, Ala and Gly;
Xaa$_{12}$ is absent or is selected from aromatic amino acid residues including Phe, Tyr and Trp;
Xaa$_{13}$ is absent or is selected from acidic amino acid residues including Glu and Asp;
Xaa$_{14}$ is absent or is selected from aromatic amino acid residues including Phe, Tyr and Trp;
Xaa$_{15}$ is absent or is selected from small amino acid residues including Ser, Thr, Ala and Gly;
Xaa$_{16}$ is absent or is selected from aromatic amino acid residues including Phe, Tyr and Trp; and
Xaa$_{17}$ is absent or is selected from small amino acid residues including Ser, Thr, Ala and Gly.

In some embodiments, Xaa$_9$ is absent or is Ser.
In some embodiments, Xaa$_{10}$ is Asp or Gly.
In some embodiments, Xaa$_{12}$ is Trp.
In some embodiments, Xaa$_{11}$ is Ala, Xaa$_{12}$ is Trp, Xaa$_{13}$ is Asp, Xaa$_{14}$ and Xaa$_{16}$ are Phe, and Xaa$_{15}$ and Xaa$_{17}$ are Thr.

In a further aspect of the invention, there is provided an isolated, synthetic or recombinant peptide comprising, consisting or consisting essentially of SEQ ID NO: 6:

[SEQ ID NO: 6]
Xaa$_9$Xaa$_{10}$CRYXaa$_2$FGXaa$_3$CEKDXaa$_5$DCCKHLGCKXaa$_6$KXaa$_8$KYC

AWDFTFT wherein:
Xaa$_9$ is absent or is selected from small amino acid residues including Ser, Thr, Ala and Gly;
Xaa$_{10}$ is selected from acidic amino acid residues including Glu and Asp, and small amino acid residues including Ser, Thr, Ala and Gly;
Xaa$_2$ and Xaa$_8$ are independently selected from hydrophobic amino acid residues including Met, Nle, Ile, Leu and Val;
Xaa$_3$ and Xaa$_5$ are independently selected from acidic amino acid residues including Glu and Asp, and small amino acid residues including Ser, Thr, Ala and Gly; and
Xaa$_6$ is selected from basic amino acid residues including Arg and Lys.

In some embodiments, Xaa$_2$, Xaa$_3$, Xaa$_5$, Xaa$_6$, Xaa$_8$, Xaa$_9$, and Xaa$_{10}$ are selected from a combination of one or more of the following:
Xaa$_2$ is Nle;
Xaa$_3$ is Asp or Gly;
Xaa$_5$ is Glu or Ala;
Xaa$_6$ is Arg or Lys;
Xaa$_8$ is Nle;
Xaa$_9$ is absent or is Ser; and
Xaa$_{10}$ is Asp or Gly.

In some embodiments, the isolated, synthetic or recombinant peptide of the invention comprises, consists or consists essentially of:

[SEQ ID NO: 7]
DCRYMFGDCEKDEDCCKHLGCKRKMKYCAWDFTFT;

[SEQ ID NO: 8]
GCRYMFGDCEKDEDCCKHLGCKRKMKYCAWDFTFT;

[SEQ ID NO: 9]
SDCRYMFGDCEKDEDCCKHLGCKRKMKYCAWDFTFT;

[SEQ ID NO: 10]
DCRYXaa$_2$FGDCEKDEDCCKHLGCKRKXaa$_8$KYCAWDFTFT;

[SEQ ID NO: 11]
DCRYMFGDCEKDEDCCKHLGCKKKMKYCAWDFTFT;

[SEQ ID NO: 12]
DCRYMFGGCEKDEDCCKHLGCKRKMKYCAWDFTFT;

[SEQ ID NO: 13]
DCRYMFGDCEKDADCCKHLGCKRKMKYCAWDFTFT;

[SEQ ID NO: 14]
DCRYMFGKCEKDEDCCKHLGCKRKMKYCAWDFTFT;

[SEQ ID NO: 15]
DCRYMFGNCEKDEDCCKHLGCKRKMKYCAWDFTFT;

[SEQ ID NO: 16]
KCRYMFGDCEKDEDCCKHLGCKRKMKYCAWDFTFT;

[SEQ ID NO: 17]
DCRYMFGDCEKDEDCCKHLGCKRRMKYCAWDFTFT;

[SEQ ID NO: 18]
DCRAMFGDCEKDEDCCKHLGCKRKMKYCAWDFTFT;

[SEQ ID NO: 19]
DCRYMFGDCKKDEDCCKHLGCKRKMKYCAWDFTFT;
or

[SEQ ID NO: 20]
DCRYMFGDCEKDKDCCKHLGCKRKMKYCAWDFTFT;

wherein Xaa$_2$ and Xaa$_8$ are Nle.

In some embodiments, the isolated, synthetic or recombinant peptide of the invention comprises, consists or consists essentially of SEQ ID NO: 7, 8, 9, 10, 11, 12 or 13, wherein Xaa$_2$ and Xaa$_8$ are Nle.

In some embodiments, the isolated, synthetic or recombinant peptide of the invention comprises, consists or consists essentially of SEQ ID NO: 7. The peptide of SEQ ID NO: 7 is designated as Pnc1a.

In some embodiments, the isolated, synthetic or recombinant peptide of the invention comprises, consists or consists essentially of SEQ ID NO: 10.

In some embodiments, the isolated, synthetic or recombinant peptide of the invention is other than a peptide consisting of the amino acid sequence of SEQ ID NO: 7 or 8.

In preferred embodiments, the peptides of the invention do not comprise methionine. Methionine residues are prone to oxidation, which can result in reduced purity and loss of activity or selectivity in solution. Suitable replacement amino acids for methionine residues may include, but are not limited to, valine, leucine, isoleucine, norleucine, norvaline, glycine or alanine; especially valine, leucine, isoleucine, norleucine or norvaline; most especially norleucine.

In some embodiments where the peptides of the present invention comprise an N- and C-terminus, the peptides of the invention have a primary, secondary or tertiary amide, a hydrazide, a hydroxamide or a free carboxyl group at the C-terminus and a primary amine or acetamide at the N-terminus. In some embodiments, the peptides of the invention are cyclic peptides and, thus, may not comprise N- or C-terminal amino acid residues.

The present invention also contemplates peptides that are variants of SEQ ID NO: 7 to SEQ ID NO: 20, especially SEQ ID NO: 7 to SEQ ID NO: 13. Such "variant" peptides include peptides derived from the peptides by deletion or addition of one or more amino acids to the N-terminal and/or C-terminal end of the peptide, deletion or addition of one or more amino acids at one or more sites in the peptide, or substitution of one or more amino acids at one or more sites in the peptide.

Variant peptides encompassed by the present invention are biologically active, that is, they continue to possess the desired biological activity of the native peptide. Such variants may result from, for example, genetic polymorphism or from human manipulation.

The peptides of SEQ ID NO: 7 to SEQ ID NO: 20, especially SEQ ID NO: 7 to SEQ ID NO: 13, may be altered in various ways, including amino acid substitutions, deletions, truncations and insertions. Methods for such manipulations are generally known in the art. For example, amino acid sequence variants of SEQ ID NO: 7 to SEQ ID NO: 20, especially SEQ ID NO: 7 to SEQ ID NO: 13, may be prepared by mutagenesis of nucleic acids encoding the amino acid sequence of SEQ ID NO: 7 to SEQ ID NO: 20, especially SEQ ID NO: 7 to SEQ ID NO: 13. Methods for mutagenesis and nucleotide sequence alterations are well known in the art. Refer to, for example, Kunkel (1985, *Proc. Natl. Acad. Sci. USA*. 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif, 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of the proteinaceous molecules of SEQ ID NO: 7 to SEQ ID NO: 20, especially SEQ ID NO: 7 to SEQ ID NO: 13. Recursive ensemble mutagenesis (REM), a technique which enhances the frequency of functional mutants in the libraries, can be used in combination with screening assays to identify active variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Variant peptides of the invention may contain conservative amino acid substitutions at various locations along their sequence, as compared to a parent (e.g. naturally-occurring or reference) amino acid sequence, such as SEQ ID NO: 7 to SEQ ID NO: 20, especially SEQ ID NO: 7 to SEQ ID NO: 13. A "conservative amino acid substitution" is one in which the amino acid residue is replaced with an amino acid residue having a similar side chain. Families of amino acid residues having similar side chains have been defined in the art as discussed in detail below.

Acidic: The residue has a negative charge due to loss of a proton at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with protons at physiological pH or within one or two pH units thereof (e.g. histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residue is charged at physiological pH and, therefore, includes amino acids having acidic or basic side chains, such as glutamic acid, aspartic acid, arginine, lysine and histidine.

Hydrophobic: The residue is not charged at physiological pH and the residue is repelled by aqueous solution so as to seek the inner positions in the conformation of a peptide in which it is contained when the peptide is in aqueous medium at physiological pH. Amino acids having a hydrophobic side chain include tyrosine, valine, isoleucine, leucine, methionine, norleucine, phenylalanine and tryptophan.

Neutral/polar: The residues are not charged at physiological pH but the residue is not sufficiently repelled by aqueous solutions so that it would seek inner positions in the conformation of a peptide in which it is contained when the peptide is in aqueous medium at physiological pH. Amino acids having a neutral/polar side chain include asparagine, glutamine, cysteine, histidine, serine and threonine.

This description also characterises certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g. PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (1992), *Science,* 256(5062): 1443-1445), however, include proline in the same group as glycine, serine, alanine and threonine. Accordingly, for the purposes of the present invention, proline is classified as a "small" amino acid.

The degree of attraction or repulsion required for classification as polar or non-polar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small amino acid residues are, of course, always non-aromatic. Dependent on their structural properties, amino acid residues may fall in two or more classes. For the naturally-occurring protein amino acids, sub-classification according to this scheme is presented in Table 1.

TABLE 1

Amino Acid Sub-Classification

| Sub-classes | Amino Acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Nonpolar/neutral | Alanine, Glycine, Isoleucine, Leucine, Methionine, Phenylalanine, Proline, Tryptophan, Valine, Norleucine |
| Polar/neutral | Asparagine, Histidine, Glutamine, Cysteine, Serine, Threonine, Tyrosine |
| Polar/negative | Aspartic acid, Glutamic acid |
| Polar/positive | Lysine, Arginine |
| Polar/large | Asparagine, Glutamine |
| Polar | Arginine, Asparagine, Aspartic acid, Cysteine, Glutamic acid, Glutamine, Histidine, Lysine, Serine, Threonine, Tyrosine |
| Hydrophobic | Tyrosine, Valine, Isoleucine, Leucine, Methionine, Phenylalanine, Tryptophan, Norleucine |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, isoleucine and norleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartic acid with a glutamic acid, a threonine with a serine, or a similar replacement of an amino acid with a structurally related amino acid will not have a major effect on the properties of the resulting variant peptide of the invention. Whether an amino acid change results in peptide that inhibits $Na_v1.7$ can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 2

Exemplary and Preferred Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |

TABLE 2-continued

Exemplary and Preferred Amino Acid Substitutions

| Original Residue | Exemplary Substitutions | Preferred Substitutions |
|---|---|---|
| Gly | Pro | Pro |
| His | Asn, Gln, Lys, Arg | Arg |
| Ile | Leu, Val, Met, Ala, Phe, Nle | Leu |
| Leu | Nle, Ile, Val, Met, Ala, Phe | Ile |
| Lys | Arg, Gln, Asn | Arg |
| Met | Leu, Ile, Phe, Nle | Nle |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Nle | Leu |

Alternatively, similar amino acids for making conservative substitutions can be grouped into three categories based on the identity of the side chains. The first group includes glutamic acid, aspartic acid, arginine, lysine and histidine, which all have charged side chains; the second group includes glycine, serine, threonine, cysteine, tyrosine, glutamine and asparagine; and the third group includes leucine, isoleucine, valine, alanine, proline, phenylalanine, tryptophan, methionine and norleucine, as described in Zubay, *Biochemistry*, third edition, Wm.C. Brown Publishers (1993).

Thus, a predicted non-essential amino acid residue in a peptide of the invention is typically replaced with another amino acid residue from the same side chain family. Alternatively, mutations can be introduced randomly along all or part of the coding sequence of a peptide of the invention, such as by saturation mutagenesis, and the resultant mutants can be screened for an activity of the parent polypeptide, as described for example herein, to identify mutants which retain that activity. Following mutagenesis of the coding sequences, the encoded peptide can be expressed recombinantly and its activity determined. A "non-essential" amino acid residue is a residue that can be altered from the wild-type sequence of an embodiment peptide of the invention without abolishing or substantially altering one or more of its activities. Suitably, the alteration does not substantially alter one of these activities, for example, the activity is at least 20%, 40%, 60%, 70% or 80% of that of the wild-type. By contrast, an "essential" amino acid residue is a residue that, when altered from the wild-type sequence of an embodiment peptide of the invention, results in abolition of an activity of the parent molecule such that less than 20% of the wild-type activity is present.

Accordingly, the present invention also contemplates variants of the peptides of any one of SEQ ID NO: 7 to SEQ ID NO: 20, especially SEQ ID NO: 7 to SEQ ID NO: 13, wherein the variants are distinguished from the parent sequence by the addition, deletion, or substitution of one or more amino acid residues. In general, variants will display at least about 80%, 81%, 82%, 83%, 84%, 85%, 86%, 87%, 88%, 89%, 90%, 91%, 92%, 93%, 94%, 95%, 96%, 97%, 98%, 99% sequence similarity to a parent or reference proteinaceous molecule sequence as, for example, set forth in any one of SEQ ID NO: 7 to SEQ ID NO: 20, especially any one of SEQ ID NO: 7 to SEQ ID NO: 13, as determined by sequence alignment programs described elsewhere herein using default parameters. Desirably, variants will have at least 80%, 81%, 82%, 83%, 84%, 85%, 86%, 87%, 88%, 89%, 90%, 91%, 92%, 93%, 94%, 95%, 96%, 97%, 98%, 99% sequence identity to a parent or reference peptide sequence as, for example, set forth in any one of SEQ ID NO: 7 to SEQ ID NO: 20, especially any one of SEQ ID NO: 7 to SEQ ID NO: 13, as determined by sequence alignment programs described herein using default parameters. Variants of any one of SEQ ID NO: 7 to SEQ ID NO: 20, especially any one of SEQ ID NO: 7 to SEQ ID NO: 13, which fall within the scope of a variant peptide of the invention, may differ from the parent molecule generally by at least 1, but by less than 8, 7, 6, 5, 4, 3, 2 or 1 amino acid residue(s). In some embodiments, a variant peptide of the invention differs from the corresponding sequence in any one of SEQ ID NO: 7 to SEQ ID NO: 20, especially any one of SEQ ID NO: 7 to SEQ ID NO: 13, by at least 1, but by less than 8, 7, 6, 5, 4, 3, 2 or 1 amino acid residue(s). The amino acid sequence of the variant peptide of the invention comprises at least six cysteine residues. In some embodiments, the amino acid sequence of the variant peptide of the invention comprises SEQ ID NO: 1, 2, 3, 4, 5 and/or 6. In particular embodiments, the variant peptide of the invention inhibits $Na_v1.7$.

If the sequence comparison requires alignment, the sequences are typically aligned for maximum similarity or identity. "Looped" out sequences from deletions or insertions, or mismatches, are generally considered differences. The differences are, suitably, differences or changes at a non-essential residue or a conservative substitution.

In some embodiments, calculations of sequence similarity or sequence identity between sequences are performed as follows:

To determine the percent identity of two amino acid sequences or of two nucleic acid sequences, the sequences are aligned for optimal comparison purposes (e.g. gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 40%, more usually at least 50% or 60%, and even more usually at least 70%, 80%, 90% or 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e. conservative substitution) at the corresponding position in the second sequence, then the molecules are similar at that position.

The percent identity between the two sequences is a function of the number of identical amino acid residues shared by the sequences at individual positions, taking into account the number of gaps and the length of each gap, which need to be introduced for optimal alignment of the two sequences. By contrast, the percent similarity between the two sequences is a function of the number of identical and similar amino acid residues shared by the sequences at individual positions, taking into account the number of gaps and the length of each gap, which need to be introduced for optimal alignment of the two sequences.

The comparison of sequences and determination of percent identity or percent similarity between sequences can be accomplished using a mathematical algorithm. In certain embodiments, the percent identity or similarity between amino acid sequences is determined using the Needleman and Wünsch, (1970, *J. Mol. Biol.*, 48: 444-453) algorithm which has been incorporated into the GAP program in the GCG software package (Devereaux, et al. (1984) *Nucleic Acids Research*, 12: 387-395), using either a Blosum 62 matrix or a PAM250 matrix, and a gap weight of 16, 14, 12, 10, 8, 6, or 4 and a length weight of 1, 2, 3, 4, 5, or 6. In some embodiments, the percent identity or similarity between amino acid sequences can be determined using the algorithm of Meyers and Miller (1989, *Cabios*, 4: 11-17) which has been incorporated into the ALIGN program (version 2.0), using a PAM120 weight residue table, a gap length penalty of 12 and a gap penalty of 4.

The present invention also contemplates an isolated, synthetic or recombinant peptide that is encoded by a polynucleotide sequence that hybridizes under stringency conditions as defined herein, especially under medium, high or very high stringency conditions, preferably under high or very high stringency conditions, to a polynucleotide sequence encoding the peptides of any one of SEQ ID NO: 7 to SEQ ID NO: 20 or the non-coding strand thereof, especially any one of SEQ ID NO: 7 to SEQ ID NO: 13 or the non-coding strand thereof. The invention also contemplates an isolated nucleic acid molecule comprising a polynucleotide sequence that hybridizes under stringency conditions as defined herein, especially under medium, high or very high stringency conditions, preferably under high or very high stringency conditions, to a polynucleotide sequence encoding the peptides of any one of SEQ ID NO: 7 to SEQ ID NO: 20 or the non-coding strand thereof, especially any one of SEQ ID NO: 7 to SEQ ID NO: 13 or the non-coding strand thereof.

As used herein, the term "hybridizes under stringency conditions" describes conditions for hybridization and washing and may encompass low stringency, medium stringency, high stringency and very high stringency conditions.

Guidance for performing hybridization reactions can be found in Ausubel, et al. (1998) Current Protocols in Molecular Biology (John Wiley and Sons, Inc.), in particular sections 6.3.1-6.3.6. Both aqueous and non-aqueous methods can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% sodium dodecyl sulfate (SDS) for hybridization at 65° C., and (i) 2× sodium chloride/sodium citrate (SSC), 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6×SSC at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In some aspects of the present invention, there is provided an isolated, synthetic or recombinant peptide of the invention that is encoded by a polynucleotide sequence that hybridizes under high stringency conditions to a polynucleotide sequence encoding the peptides of any one of SEQ ID NO: 7 to SEQ ID NO: 20 or the non-coding strand thereof, especially any one of SEQ ID NO: 7 to SEQ ID NO: 13 or the non-coding strand thereof. In certain embodiments, the isolated, synthetic or recombinant peptide of the invention is encoded by a polynucleotide sequence that hybridizes under very high stringency conditions to a polynucleotide sequence encoding the peptides of any one of SEQ ID NO: 7 to SEQ ID NO: 20 or the non-coding strand thereof, especially any one of SEQ ID NO: 7 to SEQ ID NO: 13 or the non-coding strand thereof. One embodiment of very high stringency conditions includes hybridizing 0.5 M sodium phosphate, 7% SDS at 65° C., followed by one or more washes at 0.2×SSC, 1% SDS at 65° C. The amino acid sequence of the variant peptide of the invention comprises at least six cysteine residues. In some embodiments, the amino acid sequence of the variant peptide of the invention comprises SEQ ID NO: 1, 2, 3, 4, 5 and/or 6. In particular embodiments, the variant peptide of the invention inhibits Na$_v$1.7.

Other stringency conditions are well known in the art and a person skilled in the art will recognize that various factors can be manipulated to optimize the specificity of the hybridization. Optimization of the stringency of the final washes can serve to ensure a high degree of hybridization. For detailed examples, see Ausubel, et al. (1998) Current Protocols in Molecular Biology (John Wiley and Sons, Inc.), in particular pages 2.10.1 to 2.10.16 and Sambrook, et al. (1989) Molecular Cloning: A Laboratory Manual (Cold Spring Harbour Press), in particular Sections 1.101 to 1.104.

While stringent washes are typically carried out at temperatures from about 42° C. to 68° C., a person skilled in the art will appreciate that other temperatures may be suitable for stringent conditions. Maximum hybridization rate typically occurs at about 20° C. to 25° C. below the T$_m$ for formation of a DNA-DNA hybrid. It is well known in the art that the T$_m$ is the melting temperature, or temperature at which two complementary polynucleotide sequences dissociate. Methods for estimating T$_m$ are well known in the art (see Ausubel, et al. (1998) Current Protocols in Molecular Biology (John Wiley and Sons, Inc.) at page 2.10.8). In general, the T$_m$ of a perfectly matched duplex of DNA may be predicted as an approximation by the formula:

$$T_m = 81.5 + 16.6(\log_{10} M) + 0.41(\% \, G+C) - 0.63(\% \, \text{formamide}) - (600/\text{length})$$

wherein: M is the concentration of Na$^+$, preferably in the range of 0.01 M to 0.4 M; % G+C is the sum of guanosine and cytosine bases as a percentage of the total number of bases, within the range between 30% and 75% G+C; % formamide is the percent formamide concentration by volume; length is the number of base pairs in the DNA duplex. The T$_m$ of a duplex DNA decreases by approximately 1° C. with every increase of 1% in the number of randomly mismatched base pairs. Washing is generally carried out at T$_m$−15° C. for high stringency, or T$_m$−30° C. for moderate stringency.

In one example of a hybridization procedure, a membrane (e.g. a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrrolidone and 0.1% BSA), 0.1% SDS and 200 mg/mL denatured salmon sperm DNA) containing labeled probe. The membrane is then subjected to two sequential medium stringency washes (i.e. 2×SSC, 0.1% SDS for 15 min at 45° C., followed by 2×SSC, 0.1% SDS for 15 min at 50° C.), followed by two sequential higher stringency washes (i.e. 0.2×SSC, 0.1% SDS for 12 min at 55° C. followed by 0.2×SSC and 0.1% SDS solution for 12 min at 65-68° C.

The peptides of the present invention also encompass a peptide comprising amino acids with modified side chains, incorporation of unnatural amino acid residues and/or their derivatives during peptide synthesis and the use of cross-linkers and other methods which impose conformational constraints on the peptides of the invention. Examples of side chain modifications include modifications of amino groups, such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with sodium borohydride; reductive alkylation by reaction with an aldehyde followed by reduction with sodium borohydride; substitution of disulfide bonds with diselenide bonds by replacing cysteine residues with selenocysteine residues; and trinitrobenzylation of amino groups with 2,4,6-trinitrobenzene sulfonic acid (TNBS).

The carboxyl group may be modified by carbodiimide activation through O-acylisourea formation followed by subsequent derivatization, for example, to a corresponding amide.

The guanidine group of arginine residues may be modified by formation of heterocyclic condensation products with reagents such as 2,3-butanedione, phenylglyoxal and glyoxal.

Tryptophan residues may be modified, for example, by alkylation of the indole ring with 2-hydroxy-5-nitrobenzyl bromide or sulfonyl halides, or by oxidation with N-bromosuccinimide.

Tyrosine residues may be modified by nitration with tetranitromethane to form 3-nitrotyrosine derivatives.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include, but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine, selenocysteine and/or D-isomers of amino acids. A list of unnatural amino acids contemplated by the present invention is shown in Table 3.

TABLE 3

Exemplary Unnatural Amino Acids
Non-Conventional Amino Acids

| | |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-methylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-naphthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvaline | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | L-selenocysteine |
| D-selenocysteine | L-selenomethionine |
| L-telluromethionine | L-O-methyl homoserine |
| L-S-ethyl cysteine | |

In some embodiments, the peptide of the invention comprises at least one unnatural amino acid. In particular embodiments, the peptide of the invention comprises at least one norleucine residue.

The peptides of the invention have at least six cysteine residues. Preferably, the peptides of the invention have six cysteine residues. The cysteine residues may be bonded in pairs through disulfide bonds. In some embodiments, the peptides of the invention, particularly the peptides of any one of SEQ ID NO: 1 to SEQ ID NO: 20, possess six cysteine residues bonded in pairs to form three disulfide bonds.

A large proportion of spider venom peptides comprising six cysteine residues have a cysteine connectivity between Cys I and Cys IV, Cys II and Cys V, and Cys III and Cys VI; where the six Roman numerals represent the six cysteine residues (numbered from the N-terminus). Preferably, this disulfide connectivity is present in the peptides of the present invention, especially the peptides of any one of SEQ ID NO: 1 to SEQ ID NO: 20. Accordingly, in some embodiments, the peptides of the invention comprise three disulfide bonds formed between the side chains of Cys I and Cys IV, Cys II and Cys V, and Cys III and Cys VI; wherein Cys I represents the cysteine residue corresponding to the first cysteine residue in SEQ ID NO: 1, Cys II represents the cysteine residue corresponding to the second cysteine residue in SEQ ID NO: 1, Cys III represents the cysteine residue corresponding to the third cysteine residue in SEQ ID NO: 1, Cys IV represents the cysteine residue corresponding to the fourth cysteine residue in SEQ ID NO: 1, Cys V represents the cysteine residue corresponding to the fifth cysteine residue in SEQ ID NO: 1, and Cys VI represents the cysteine residue corresponding to the sixth cysteine residue in SEQ ID NO: 1 (numbered from the N-terminus). For example, Cys I refers to Cys 3 in SEQ ID NO: 2, Cys II refers to Cys 10 in SEQ ID NO: 2, Cys III refers to Cys 16 in SEQ ID NO: 2, Cys IV refers to Cys 17 in SEQ ID NO: 2, Cys V refers to Cys 22 in SEQ ID NO: 2, and Cys VI refers to Cys 29 in SEQ ID NO: 2 (numbered from the N-terminus).

Without wishing to be bound by theory, this disulfide bond connectivity forms an inhibitor cysteine knot motif in which a ring formed by two of the disulfide bonds and the intervening sections of the peptide backbone is pierced by the third disulfide bond. Peptides comprising an inhibitor cystine knot motif have high levels of chemical and thermal stability, which may be advantageous for therapeutic use.

Peptides comprising an inhibitor cystine knot motif possess at least four loops formed by at least three disulfide bonds. Each loop comprises a peptide backbone with a varied number of amino acids. For example, the peptide backbone between Cys I and II (loop 1) may comprise about 2 to about 7 amino acid residues, the peptide backbone between Cys II and Cys III (loop 2) may comprise about 3 to about 11 amino acid residues, the peptide backbone between Cys III and Cys IV (loop 3) may comprise about 0 to about 7 amino acid residues, the peptide backbone between Cys IV and Cys V (loop 4) may comprise about 1 to about 17 amino acid residues and the peptide backbone between Cys V and Cys VI (loop 5) may comprise about 1 to about 19 amino acid residues. Accordingly, the present invention also contemplates variant peptides of the invention that differ from the amino acid sequence of any one of SEQ ID NO: 1 to SEQ ID NO: 20 by the insertion of one or more amino acid residues in any one of loops 1 to 5. In some embodiments, the variant peptide of the invention comprises the insertion of 1 amino acid residue between Cys I and Cys II; the insertion of 1, 2, 3, 4, 5 or 6 amino acid residues between Cys II and Cys III; the insertion of 1, 2, 3, 4, 5, 6 or 7 amino acid residues between Cys III and Cys IV; the insertion of 1, 2, 3, 4, 5, 6, 7 or 8 amino acid residues between Cys IV and Cys V; and/or the insertion of 1, 2, 3, 4, 5, 6, 7 or 8 amino acid residues between Cys V and Cys VI (starting at the N-terminus); wherein the amino acid residues may be selected from any amino acid residue and are inserted at any position in the amino acid sequence between the two designated cysteine residues.

The present invention also contemplates variant peptides of the invention that differ from the amino acid sequence of any one of SEQ ID NO: 1 to SEQ ID NO: 20 by the deletion of one or more amino acid residues in any one of loops 1 to 5. In some embodiments, the variant peptide of the invention comprises the deletion of 1, 2, 3 or 4 amino acid residues between Cys I and Cys II; the deletion of 1 or 2 amino acid residues between Cys II and Cys III; the deletion of 1, 2 or 3 amino acid residues between Cys IV and Cys V; and/or the deletion of 5, 4, 3, 2 or 1 amino acid residues between Cys V and Cys VI (starting at the N-terminus); wherein any amino acid residue may be deleted between the two designated cysteine residues.

In some embodiments, one or more of the disulfide bonds of the peptides of the invention are replaced with a suitable alternative, such as a diselenide bond, a seleno-sulfur bond, a thioether bond such as a lanthionine bond, a selenoether bond, a triazole bond, a lactam bond or a dimethylene bond. In particular embodiments, at least two cysteine residues are substituted with selenocysteine residues. The selenocysteine residues in the sequences must be positioned such that when the peptide is oxidised, a diselenide bond is produced between the side chains of two selenocysteine residues.

Additional amino acids or other substituents may be added to the N- or C-termini, if present, of the peptides of the present invention. For example, the peptides of the present invention may form part of a longer sequence with additional amino acids added to either or both of the N- and C-termini.

In some embodiments, the peptides of the present invention comprise a stabilising moiety. The stabilising moiety may be conjugated at any point on the peptide. Suitable stabilising moieties include, but are not limited to, polyethylene glycol (PEG), a glycan or a capping moiety, including an acetyl group, pyroglutamate or pyroglutamine, or an amino group. In preferred embodiments, the acetyl group and/or pyroglutamate or pyroglutamine are conjugated to the N-terminal amino acid residue of the peptide. In particular embodiments, the N-terminus of the peptide is an acetamide. In preferred embodiments, the amino group is conjugated to the C-terminal amino acid residue of the peptide. In particular embodiments, the peptide has a primary, secondary or tertiary amide, a hydrazide or a hydroxamide at the C-terminus; particularly a primary amide at the C-terminus. In preferred embodiments, the PEG is conjugated to the N-terminal or C-terminal amino acid residue of the peptide or through the amine of a lysine side-chain or other suitably modified side-chain, especially through the N-terminal amino acid residue or through the amine of a lysine side-chain.

In preferred embodiments, the peptides of the present invention have a primary amide or a free carboxyl group at the C-terminus and a primary amine or acetamide at the N-terminus.

In some embodiments, the peptides of the present invention comprise a membrane permeating moiety. The membrane permeating moiety may be conjugated at any point on the peptide. In preferred embodiments, the membrane permeating moiety is a lipid moiety, such as a $C_{10}$-$C_{20}$ fatty acyl group, especially hexadecanoyl (palmitoyl; $C_{16}$) or tetradecanoyl (myristoyl; $C_{14}$); most especially tetradecanoyl. In preferred embodiments, the membrane permeating moiety is conjugated to the N- or C-terminal amino acid residue or through the amine of a lysine side-chain of the peptide or other suitably modified side-chain, especially the N-terminal amino acid residue of the peptide or through the amine of a lysine side-chain.

In some embodiments, the peptides of the present invention are cyclic peptides. Without wishing to be bound by theory, cyclisation of peptides is thought to decrease the susceptibility of the peptides to degradation. In particular embodiments, the peptides are cyclised using N-to-C cyclisation (head to tail cyclisation), preferably through an amide bond. Such peptides do not possess N- or C-terminal amino acid residues. In particular embodiments, the peptides have an amide-cyclised peptide backbone. In other embodiments, the peptides are cyclised using side-chain to side-chain cyclisation, preferably through a disulfide bond a diselenide bond, a seleno-sulfur bond, a thioether bond such as a lanthionine bond, a selenoether bond, a triazole bond, a lactam bond or a dimethylene bond; especially through a disulfide bond.

In some embodiments, the N- and C-termini are linked using a linking moiety. The linking moiety may be a peptide linker such that cyclisation produces an amide-cyclised peptide backbone. Variation within the peptide sequence of the linking moiety is possible, such that the linking moiety may be modified to alter the physicochemical properties of the peptides and potentially reduce side effects of the peptides of the invention or otherwise improve the therapeutic use of the peptides, for example, by improving stability. The linking moiety will be of suitable length to span the distance between the N- and C-termini of the peptide without substantially altering the structural conformation of the peptide, for example, a peptidic linking moiety may be between 2 and 10 amino acid residues in length. In some embodiments, longer or shorter peptidic linking moieties may be required.

The peptides of the present invention may be in the form of salts or prodrugs. The salts of the peptides of the present invention are preferably pharmaceutically acceptable, but it will be appreciated that non-pharmaceutically acceptable salts also fall within the scope of the present invention.

The peptides of the present invention may be in crystalline form and/or in the form of solvates, for example, hydrates. Solvation may be performed using methods known in the art.

In a further aspect of the present invention, there is provided an isolated nucleic acid molecule comprising a polynucleotide sequence that encodes the peptide of the invention or is complementary to a polynucleotide sequence that encodes a peptide of the invention.

The isolated nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules are typically isolated, in some embodiments, the nucleic acid molecules may be integrated into or ligated to or otherwise fused or associated with other genetic molecules, such as an expression vector. Generally, an expression vector includes transcriptional and translational regulatory nucleic acid operably linked to the polynucleotide sequence.

In a further aspect of the present invention, there is provided a genetic construct for expressing the nucleic acid molecules. Such constructs typically comprise a nucleic acid molecule as described above operably linked to a regulatory sequence.

The peptides of the present invention may be prepared using recombinant DNA techniques or by chemical synthesis.

In some embodiments, the peptides of the present invention are prepared using standard peptide synthesis methods, such as solution synthesis or solid phase synthesis, followed by oxidative disulfide bond formation. The chemical synthesis of the peptides of the invention may be performed manually or using an automated synthesiser. For example, the linear peptides may be synthesised using solid phase peptide synthesis using either Boc or Fmoc chemistry, as described in Merrifield (1963) *J Am Chem Soc,* 85(14): 2149-2154; Schnolzer, et al. (1992) *Int J Pept Protein Res,* 40: 180-193 and Cardoso, et al. (2015) *Mol Pharmacol,* 88(2): 291-303. Following deprotection and cleavage from the solid support, the linear peptides are purified using suitable methods, such as preparative chromatography. The purified linear peptides are then oxidised in buffered systems to form the disulfide bonds, followed by purification using a suitable means, such as preparative chromatography. Alternatively, a synthetic method involving selective disulfide bond formation may be used as described in, for example, Kent, et al. (1998) *Biopolymers,* 46: 53-63.

In other embodiments, the peptide may be cyclised. Cyclisation may be performed using several techniques, as described in, for example, Davies (2003) *J Pept Sci,* 9: 471-501. In particular embodiments, the linear peptide is synthesised using solid phase peptide synthesis involving Boc-chemistry, starting with a cysteine residue at the N-terminus and ending with a thioester at the C-terminus. Following deprotection and cleavage from the resin, the peptide is cyclised via a thiolactone intermediate, which subsequently rearranges to an amine-cyclised peptide. The reduced peptide is then oxidised to form the disulfide bonds.

Disulfide bond replacement with diselenide, seleno-sulfur, thioether such as lanthionine, selenoether, triazole, lactam or dimethylene bonds may be prepared using methods known in the art, for example, as described in Muttenthaler and Alewood (2008) *J Pept Sci,* 14(12): 1223-1239; Li, et al. (2002) *Current Organic Chemistry,* 6: 411-440; and Fazio, et al. (2005) *Biopolymers (Peptide Science),* 84(2): 205-218.

In some embodiments, the peptides of the present invention are prepared using recombinant DNA techniques. For example, the peptides of the invention may be prepared by a procedure including the steps of: (a) preparing a construct comprising a polynucleotide sequence that encodes the peptide of the invention and that is operably linked to a regulatory element; (b) introducing the construct into a host cell; (c) culturing the host cell to express the polynucleotide sequence to thereby produce the encoded peptide of the invention; and (d) isolating the peptide of the invention from the host cell. The peptide of the present invention may be prepared recombinantly using standard protocols, for example, as described in Klint, et al. (2013) *PLOS One,* 8(5): e63865; Sambrook, et al. (1989) Molecular Cloning: A Laboratory Manual (Cold Spring Harbour Press), in particular Sections 16 and 17; Ausubel, et al. (1998) Current Protocols in Molecular Biology (John Wiley and Sons, Inc.), in particular Chapters 10 and 16; and Coligan, et al. (1997) Current Protocols in Protein Science (John Wiley and Sons, Inc.), in particular Chapters 1, 5 and 6. Under some circumstances it may be desirable to undertake oxidative bond formation of the expressed peptide after peptide expression. This may be preceded by a reductive step to provide the linear peptide. Suitable conditions for reduction and oxidation of the peptide will be readily determined by a person skilled in the art.

In some embodiments, the peptides of the present invention may be in the form of a pharmaceutical composition, wherein the pharmaceutical composition comprises a peptide of the invention and a pharmaceutically acceptable carrier or diluent.

The peptide of the invention may be formulated into the pharmaceutical composition as neutral or salt forms.

As will be appreciated by those skilled in the art, the choice of pharmaceutically acceptable carrier or diluent will be dependent on the route of administration and on the nature of the condition and the subject to be treated. The particular carrier or delivery system and route of administration may be readily determined by a person skilled in the art. The carrier or delivery system and route of administration should be carefully selected to ensure that the activity of the peptide is not depleted during preparation of the formulation and the peptide is able to reach the site of action intact. The pharmaceutical compositions of the present invention may be administered through a variety of routes, including, but not limited to, intravenous, intramuscular, intraperitoneal, subcutaneous, intracerebral, intracerebroventricular, intrathecal, epidural, topical, transdermal, oral, intranasal or inhalation administration; especially topical, transdermal, intravenous or intraperitoneal administration; most especially intravenous or intraperitoneal administration.

The pharmaceutical forms suitable for injectable use include sterile injectable solutions or dispersions and sterile powders for the preparation of sterile injectable solutions. The pharmaceutical forms suitable for intranasal or inhalation delivery include solutions, dry powders, suspensions or emulsions. Such forms should be stable under the conditions of manufacture and storage and may be preserved against reduction, oxidation and microbial contamination.

A person skilled in the art will readily be able to determine appropriate formulations for the peptides of the present invention using conventional approaches. Techniques for formulation and administration may be found in, for example, Remington (1980) Remington's Pharmaceutical Sciences, Mack Publishing Co., Easton, Pa., latest edition. Identification of preferred pH ranges and suitable excipients, such as antioxidants, is routine in the art, for example, as described in Katdare and Chaubel (2006) Excipient Development for Pharmaceutical, Biotechnology and Drug Delivery Systems (CRC Press). Buffer systems are routinely used to provide pH values of a desired range and may include, but are not limited to, carboxylic acid buffers, such as acetate, citrate, lactate, tartrate and succinate; glycine; histidine; phosphate; tris(hydroxymethyl)aminomethane (Tris); arginine; sodium hydroxide; glutamate; and carbonate buffers. Suitable antioxidants may include, but are not limited to, phenolic compounds such as butylated hydroxytoluene (BHT) and butylated hydroxyanisole; vitamin E; ascorbic acid; reducing agents such as methionine or sulphite; metal chelators such as ethylene diamine tetraacetic acid (EDTA); cysteine hydrochloride; sodium bisulfite; sodium metabisulfite; sodium sulphite; ascorbyl palmitate; lecithin; propyl gallate; and alpha-tocopherol.

The solvent or dispersion medium may contain any of the conventional solvent or carrier systems for peptide actives and may contain, but is not limited to, water; ethanol; polyols, such as glycerol, propylene glycol and polyethylene glycol; vegetable oils; dimethylacetamide; N-methyl-2-pyrrolidone; dimethylsulfoxide; and combinations thereof.

The pharmaceutical compositions of the present invention may comprise, but are not limited to, preservatives including parabens, chlorobutanol, phenol, sorbic acid, thiomersal, benzalkonium chloride, phenyl ethyl alcohol, EDTA, benzyl alcohol or combinations thereof; agents that prolong absorption such as aluminium monostearate or gelatine; solubilising agents such as ethylene diamine dihydrochloride or polyvinylpyrrolidone; humectants such as sorbitol, glycerol or mannitol; mucoadhesive agents such as polyacrylic acids, xanthan gum, carboxymethylcellulose, hydroxypropyl cellulose, hydroxypropylmethyl cellulose, carrageenan, alginates or chitosan; viscosity modifiers such as propylene glycol, polyethylene glycol or glycerol; surfactants such as oleic acid, polysorbates, Tween, polyvinylpyrrolidone, lecithin or sorbitane trioleate; stabilising agents such as albumin, leucine, sugars e.g. sucrose, lactose, trehalose, dextrose or raffinose, or polyols such as mannitol or sorbitol; antiadherants such as magnesium stearate; osmolality adjusting agents such as sugar or sodium chloride; or combinations thereof. In some embodiments, the pharmaceutical composition is isotonic with blood.

Injectable pharmaceutical forms may be delivered by any appropriate route, including intravenous, intramuscular, intraperitoneal, subcutaneous, intracerebral, intracerebroventricular, intrathecal or epidural injection or infusion; particularly intraperitoneal or intravenous injection or infusion. In some embodiments, the pharmaceutical composition is formulated for intraperitoneal or intravenous administration.

Intranasal formulations may be administered in the form of a spray, drop or syringe; especially a spray.

Inhalation formulations may be administered in the form of an aerosol spray from a pressurised dispenser or container, which contains a propellant such as carbon dioxide gas, dichlorodifluoromethane, nitrogen, propane, hydrofluoroalkane or other suitable gas or combination of gases; or using a nebuliser.

The peptides of the invention may be incorporated into modified-release preparations and formulations, for example, polymeric microsphere formulations, or oil- or gel-based formulations.

Sterile solutions may be prepared by combining the active compounds in the required amount in the appropriate solvent with other excipients as described above as required, followed by sterilisation, such as filtration. Generally, dispersions are prepared by incorporating the various sterilised active compounds into a sterile vehicle which contains the basic dispersion medium and the required excipients as described above. Sterile dry powders may be prepared by vacuum- or freeze-drying a sterile solution comprising the active compounds and other required excipients as described above.

With suitable stabilisation, for example, N-to-C cyclisation, the peptides of the invention may be administered through oral routes of administration. Accordingly, other formulations for administration are contemplated by the present invention, including tablets, troches, capsules, elixirs, suspensions, syrups or wafers for oral delivery. Suitable components for such formulations are well known in the art.

The peptides of the invention may also be administered through topical routes of administration. Accordingly, the peptides of the invention may be formulated for topical administration including, but not limited to, as a cream, foam, gel, ointment, lotion or spray, or in a dressing. Suitable components for such formulations are well known in the art.

The peptides of the invention may also be administered transdermally. Accordingly, the peptides of the invention may be administered using a transdermal patch, a microneedle, or other suitable techniques, for example, the techniques discussed in Prausnitz and Langer (2008) *Nat Biotechnol,* 26(11): 1261-1268. In some embodiments, the peptides of the invention may be administered in the form of a transdermal gel. A skilled person will be well aware of suitable components for transdermal formulations.

Pharmaceutically acceptable vehicles and/or diluents include any and all solvents, dispersion media, coatings, antimicrobial agents, isotonic and absorption delaying agents. A skilled person would be familiar with suitable agents. Additional active ingredients may also be incorporated into the pharmaceutical compositions. In some embodiments, the pharmaceutical composition further comprises an agent that inhibits $Na_v1.7$, an agent that has analgesic activity, or an anaesthetic, antipruritic, antitussive or anti-inflammatory agent.

It is advantageous to formulate the compositions in dosage unit form for ease of administration and uniformity of dosage. The determination of the novel dosage unit forms of the present invention is dictated by and directly dependent on the unique characteristics of the active material, the particular therapeutic effect to be achieved and the limitations inherent in the art of compounding active materials for the treatment of disease in living subjects having a diseased condition in which bodily health is impaired as herein disclosed in detail.

As mentioned above, the active peptide is compounded for convenient and effective administration in effective amounts with a suitable pharmaceutically acceptable carrier in dosage unit form. In some embodiments, a unit dosage form may comprise the active peptide of the invention in amount in the range of from about 0.25 m to about 2000 mg. The active peptide of the invention may be present in an amount of from about 0.25 µg to about 2000 mg/mL of carrier. In embodiments where the pharmaceutical composition comprises one or more additional active ingredients, the dosages are determined by reference to the usual dose and manner of administration of the said ingredients.

3. Methods

In accordance with the present invention, the peptides of the invention are useful in methods for the treatment or prevention of conditions associated with $Na_v1.7$ activity, particularly conditions in respect of which inhibition of $Na_v1.7$ activity is associated with effective treatment. Thus, the peptides of the invention are useful for the treatment or prevention of conditions such as itch, cough or pain.

In one aspect of the present invention, there is provided a method of inhibiting $Na_v1.7$, comprising contacting a $Na_v1.7$ expressing cell with a peptide of the invention.

In some embodiments, the peptides of the invention selectivity inhibit $Na_v1.7$ over at least one other subtype of voltage gated sodium channel, particularly $Na_v1.4$, $Na_v1.5$ and $Na_v1.6$. In some embodiments, the peptides of the invention selectively inhibit $Na_v1.7$ over the other eight subtypes of voltage gated sodium channel ($Na_v1.1$-$Na_v1.6$, $Na_v1.8$ and $N_v1.9$). In some embodiments, the peptides of the invention exhibit $Na_v1.7$ selectivity of greater than about 2-fold, 5-fold, 10-fold, 20-fold, 50-fold, 100-fold or greater than about 500-fold with respect to inhibiting one or more other voltage gated sodium channel subtypes, or with respect to each of the other eight voltage gated sodium channel subtypes ($Na_v1.1$-$Na_v1.6$, $Na_v1.8$ and $Na_v1.9$).

Without wishing to be bound by theory, it is thought that the selective inhibition of $Na_v1.7$ over other voltage gated sodium channel subtypes will avoid the adverse effects associated with non-selective inhibition. Furthermore, it is thought that inhibition of $Na_v1.7$ will not produce the adverse effects commonly associated with the use of analgesics, including cognitive and gastrointestinal effects, the production of respiratory depression, tolerance and addiction.

The present invention also provides a peptide of the invention for use in inhibiting $Na_v1.7$. In another aspect of the invention, there is provided a use of a peptide of the invention for inhibiting $Na_v1.7$. The present invention contemplates the use of a peptide of the invention in the manufacture of a medicament for inhibiting $Na_v1.7$.

In another aspect of the present invention, there is provided a method of treating or preventing a condition in respect of which inhibition of $Na_v1.7$ is associated with effective treatment, comprising administration of a peptide of the invention. In particular embodiments, the peptide is administered to a subject in need of such treatment, although the peptide may be administered prophylactically. In particular embodiments, the subject is a mammal, especially a human.

The present invention also provides the use of a peptide of the invention in the manufacture of a medicament for treating or preventing a condition in respect of which inhibition of $Na_v1.7$ is associated with effective treatment. In another aspect of the invention, there is provided the use of a peptide of the invention for treating or preventing a condition in respect of which inhibition of $Na_v1.7$ is associated with effective treatment. In still another aspect of the invention, there is provided a peptide of the invention for use in treating or preventing a condition in respect of which inhibition of $Na_v1.7$ is associated with effective treatment.

The conditions in which inhibition of $Na_v1.7$ is associated with effective treatment may include, but are not limited to, itch, cough or pain, including neuropathic, inflammatory or nociceptive pain. The condition in which inhibition of $Na_v1.7$ is associated with effective treatment may include, but is not limited to, inherited erythromelalgia, paroxysmal extreme pain disorder or peripheral neuropathy.

Types of neuropathic pain which may be treated or prevented using a peptide of the invention may include, but is not limited to, peripheral neuropathy; diabetic neuropathy; post herpetic neuralgia; trigeminal neuralgia; back pain; cancer neuropathy; HIV neuropathy; phantom limb pain; carpal tunnel syndrome; paroxysmal extreme pain disorder; central post-stroke pain; post-operative pain; erythromelalgia (also known as erythermalgia) such as inherited erythromelalgia; or pain associated with chronic alcoholism, hypothyroidism, uraemia, multiple sclerosis, spinal cord injury, Parkinson's disease, epilepsy or vitamin deficiency.

Types of inflammatory pain which may be treated or prevented using a peptide of the invention may include, but is not limited to, arthritic pain, including pain associated with rheumatoid arthritis, osteoarthritis, rheumatoid disease, degenerative joint disease, gout or ankylosing spondylitis; or visceral pain, including pain associated with inflammatory bowel disease, functional bowel disorder, gastroesophageal reflux, dyspepsia, functional abdominal pain syndrome, Crohn's disease, ileitis, ulcerative colitis, endometriosis, dysmenorrhea, painful bladder syndrome, prostatitis, cystitis, pancreatitis or pelvic pain.

Types of nociceptive pain which may be treated or prevented using a peptide of the invention may include, but is not limited to, pain associated with central nervous system trauma, strains, sprains, burns, myocardial infarction or acute pancreatitis; post-operative pain; posttraumatic pain; renal colic; cancer pain including tumour related pain or pain associated with cancer therapy; or back pain, including pain associated with herniated or ruptured intervertebral discs, or pain associated with abnormalities of the lumber facet joints, sacroiliac joints, paraspinal muscles or the posterior longitudinal ligament.

Other types of pain in which administration of the peptides of the invention may be useful include, but is not limited to, pain resulting from musculoskeletal disorders, including myalgia, fibromyalgia, spondylitis, sero-negative arthropathies, non-articular rheumatism, dystrophinopathy, glycogenolysis, polymyositis or pyomyositis; heart or vascular pain, including pain resulting from angina, myocardial infarction, mitral stenosis, pericarditis, Raynaud's phenomenon, scleredoma or skeletal muscle ischemia; head pain including migraine, cluster headache, tension-type headache, mixed headache or headache associated with vascular disorders; breakthrough pain; or orofacial pain, including dental pain, otic pain, burning mouth syndrome or temporomandibular myofascial pain.

In some embodiments, the peptide of the invention may be used for treating or preventing inherited erythromelalgia, paroxysmal extreme pain disorder or peripheral neuropathy.

In some embodiments, the peptide of the invention may be used for treating or preventing pain. In some embodiments, the pain is selected from neuropathic, inflammatory and nociceptive pain.

In some embodiments, the peptide of the invention may be used for treating or preventing cough or itch. The itch may be, but is not limited to, chronic itch, acute itch, histamine-dependent itch or histamine-independent itch. The acute itch may be mediated or induced by gastrin-releasing peptide and may be mediated in superficial dorsal horn neurons. The chronic itch may be, but is not limited to, itch associated with atopic dermatitis, allergic contact dermatitis, psoriasis, renal disease, liver disease, zoster virus or eczema.

The cough may be, but is not limited to, pathological or chronic cough. In particular embodiments, the cough is non-productive cough, such as a dry cough. In some embodiments, the cough is non-productive cough in a subject suffering from idiopathic pulmonary fibrosis.

In some embodiments, the peptide of the invention may suppress or reduce cough. In some embodiments, the peptide of the invention may suppress or reduce itch.

In another aspect of the invention, there is provided a method of treating neuropathic pain, inflammatory pain or nociceptive pain comprising administration of a peptide of the invention to a subject in need thereof.

In another aspect of the invention, there is provided a method of treating or preventing neuropathic pain, inflammatory pain or nociceptive pain comprising administration of a peptide of the invention to a subject.

While the peptide of the invention may be the sole active agent administered to the subject, the administration of other active agents is within the scope of the invention. For example, the peptide of the invention may be administered with one or more therapeutic agents, such as other agents that inhibit $Na_v1.7$ or that have analgesic activity, or anaesthetic, antipruritic, antitussive or anti-inflammatory agents. The peptide of the invention and the one or more therapeutic agents may be administered separately, simultaneously or sequentially.

In some embodiments, the peptide of the invention may be administered with an agent that has analgesic activity. The peptide of the invention and the agent that has analgesic activity may be administered separately, simultaneously or sequentially. Accordingly, the present invention also contemplates compositions comprising a peptide of the invention, an agent that has analgesic activity and a pharmaceutically acceptable carrier or diluent.

The agent that has analgesic activity may be any agent that is capable of providing analgesia alone and/or when combined with the peptide of the invention. Accordingly, the agent that has analgesic activity may include, but is not limited to, an opioid analgesic such as oxycodone, morphine, pethidine, codeine, hydrocodone, dihydrocodeine, dihydromorphine, fentanyl, buprenorphine, butorphanol, hydromorphone, levallorphan, levorphanol, meperidine, methadone, nalmefene, nalorphine, naloxone, naltrexone, nalbuphine, oxymorphone, tapentadol, tramadol, propoxyphene, ketobemidone or pentazocine; a non-steroidal anti-inflammatory drug such as acetylsalicylic acid, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin, zomepirac, celecoxib, deracoxib, etoricoxib, mavacoxib or parecoxib; paracetamol; flupirtine; nefopam; retigabine; duloxetine; promethazine; carisoprodol; an anticonvulsant-type analgesic including pregabalin, gabapentin, gabapentin enacarbil, carbamazepine, topiramate or lamotrigine; a tricyclic antidepressant such as clomipramine, amitriptyline, desipramine, imipramine, doxepin or nortriptyline; an antidepressant such as trazodone, duloxetine or milnacipran; an enkephalinase inhibitor such as phosphoramidon, racecadotril, bestatin, N-([(R,S)-2-benzyl-3 [(S)(2-amino-4-methylthio)butyldithio]-1-oxopropyl)-L-phenylalanine benzyl ester (RB101), RB3007, N—((S)-2-benzyl-3 [(S)-2-amino-4-methylthio)butyldithi-]-1-oxopropyl)-L-alanine benzyl ester (RB120), opiorphin, thiorphin, kelatorphan, D-phenylalanine, tynorphin or spinorphin; opioid peptides such as an endorphin, an enkephalin, a dynorphin, adrenorphin, amidorphin, an endomorphin, a hemorphin, a rubiscolin, a casomorphin, a deltorphin or a dermorphin; a barbiturate such as amobarbital, aprobarbital, butabital, mephobarbital, methohexital, pentobarbital, phenobarbital, secobarbital or thiopental; an NMDA receptor antagonist such as dextromethorphan, ketamine, neramexane or memantine; an alpha-adrenergic such as clonidine, guanfacine or dexmedetomidine; a tachykinin antagonist such as aprepitant or maropitant; a muscarinic acetylcholine receptor antagonist such as oxybutynin, propiverine, trospium, flavoxate, darifenacin, solifenacin, temaverine or ipratropium; a nicotinic acetylcholine receptor agonist such as varenicline, tebanicline or nicotine; a transient receptor potential vanilloid type 1 (TRPV1) receptor agonist such as resiniferatoxin or capsaicin; a TRPV1 receptor antagonist such as capsazepine or mavatrep; a transient receptor potential ankyrin 1 (TRPA1) receptor agonist such as cinnemaldehyde; a TRPA1 receptor antagonist such as GRC 17536, CB-625, mecamylamine, 4-nitro-N-(2,2,2-trichloro-1-((4-chlorophenyl)sulfanyl)ethyl)benzamide (AMG2504), 4-methoxy-N-(2,2,2-trichloro-1-((4-chlorophenyl)sulfanyl)ethyl)benzamide (AMG5445), 4-bromo-N-(2,2,2-trichloro-1-((4-chlorophenyl)sulfanyl) ethyl)benzamide (AMG7160), N-(2,2,2-trichloro-1-((4-chlorophenyl)sulfanyl)ethyl)benzamide (AMG9090), 4-methyl-N-[2,2,2-trichloro-1-(4-nitro-phenyl sulfanyl)-ethyl]-benzamide (CMP1), 4-methyl-N-[2,2,2-trichloro-1-(4-chlorophenyl sulfanyl)ethyl]benzamide (CMP2), N-[2,2,2-trichloro-1-(4-chlorophenyl sulfanyl)ethyl]acetamide (CMP3), 1,2,3,6-tetrahydro-1,3-dimethyl-N-[4-(1-methylethyl)phenyl]-2,6-dioxo-7H-purine-7-acetamide (HC-030031), 2-(1,3-dimethyl-2,6-dioxo-1,2,3,6-tetrahydro-7H-purin-7-yl)-N-[4-(1-methylpropyl)phenyl]acetamide (Chembridge-5861528), 4-(4-chlorophenyl)-3-methylbut-3-en-2-oxime (AP-18), or (1E,3E)-1-(4-fluorophenyl)-2-methyl-1-penten-3-one oxime (A-967079); a transient receptor potential vanilloid subtype 3 (TRPV3) receptor antagonist such as GRC 15300 (SAR292833); a corticosteroid such as dexamethasone; a serotonin receptor agonist such as eletriptan, sumatriptan, naratriptan, solmitriptan or rizatriptan; a phosphodiesterase type 5 (PDE5) inhibitor such as sildenafil, tadalafil or vardenafil; a muscle relaxant such as diazepam, lorazepam, methocarbamol, cyclobenzaprine, metaxalone, tizanidine or baclofen; a serotonin reuptake inhibitor such as sertraline, desmethylsertraline, fluoxetine, norfluoxetine, fluvoxamine, paroxetine, citalopram, desmethylcitalopram, escitalopram, fenfluoramine, femoxetine, ifoxetine, cyanodothiepin, litoxetine, dapoxetine, nefazodone, cericlamine or trazodone; a noradrenaline reuptake inhibitor such as maprotiline, reboxetine, lofepramine, mirtazapine, oxaprotiline, fezolamine, tomoxetine, mianserin, buprorion, hydroxybuproprion, nomifensine or viloxazine; a serotonin and noradrenaline reuptake inhibitor such as venlafaxine, desvenlafaxine, clomipramine, desmethylclomipramine, duloxetine, milnacipran or imipramine; a 5-lipoxygenase inhibitor such as esculetin or zileuton; a calcium channel blocker such as ziconotide or ethosuximide; a sodium channel modulator such as bupivacaine, lidocaine, mexiletine or phenytoin; or salts, prodrugs or combinations thereof.

In particular embodiments, the agent that has analgesic activity is an opioid analgesic, preferably morphine, buprenorphine, fentanyl or oxycodone.

Without wishing to be bound by theory, the administration of a peptide of the invention with an agent that has analgesic activity may provide a greater analgesic effect than either component administered alone and, thus, may enable lower doses of each component to be administered to a subject.

In some embodiments, the peptide of the invention may be administered with one or more therapeutic agents, such as other agents that inhibit $Na_v1.7$ or that have analgesic activity, or anaesthetic, antipruritic, antitussive or anti-inflammatory agents.

Suitable agents that inhibit $Na_v1.7$ may include, but are not limited to, GDC-0310, GDC-0276 (RG7893), Phlotoxin-1, μ-SLPTX-Ssm6a, GpTx-1, Huwentoxin-IV, ProTx-II, 4-[2-(3-amino-1H-pyrazol-4-yl)-4-chlorophenoxy]-5-chloro-2-fluoro-N-4-thiazolyl-benzenesulfonamide 4-methylbenzenesulfonate (PF-05089771), N-[6-amino-5-(2-chloro-5-methoxyphenyl)-2-pyridinyl]-1-methyl-1H-pyrazole-5-carboxamide (PF-04531083), DSP-2230, N-[(3S)-3,4-dihydro-5-(5-methoxy-2-pyrazinyl)-2H-1-benzopyran-3-yl]-6-[(2,2,2-trifluoroethoxy)methyl]-3-pyridinecarboxamide (AZD-3161), NKTR-171, raxatrigine (CNV1014802), funapide (XEN402), CC8464, CNV3000223, CNV3000164, antibodies described in WO 2015/035173 A1, or compounds described in WO 2015/102929 A1, WO 2012/125973 A2, WO 2016/009303 A1, WO 2009/012242 A2, EP 2593427 A1, or salts, prodrugs or combinations thereof. The contents of the publications listed above are herein incorporated by reference in their entirety.

Suitable anaesthetic agents may include, but are not limited to, procaine, amethocaine, lidocaine, prilocaine, bupivacaine, levobupivacaine, ropivacaine, mepivacaine, dibucaine, benzocaine, tetracaine, etidocaine, desflurane, enflurane, halothane, isoflurane, methoxyflurane, nitrous oxide, sevoflurane, barbiturates, benzodiazepines, etomidate, ketamine, propofol, or salts, prodrugs or combinations thereof.

Suitable antipruritic agents may include, but are not limited to, antihistamines such as diphenhydramine; corticosteroids such as hydrocortisone; counterirritants such as mint oil, menthol or camphor; nalfurafine; or salts, prodrugs or combinations thereof.

Suitable antitussive agents may include, but are not limited to, codeine, pholcodine, dextromethorphan, noscapine, butamirate, or salts, prodrugs or combinations thereof.

The peptide of the invention may be administered by an appropriate route including, but not limited to, intravenous, intramuscular, intraperitoneal, subcutaneous, intracerebral, intracerebroventricular, intrathecal, epidural, topical, transdermal, oral, intranasal or inhalation administration; especially topical, transdermal, intravenous or intraperitoneal administration; most especially intravenous or intraperitoneal administration.

A skilled person would be well aware of suitable assays used to assess $Na_v1.7$ inhibition and to identify peptides that inhibit $Na_v1.7$, for example, the assays described in in Jeffrey, et al. (2006) Expression and Analysis of Recombinant Ion Channels (WILEY-VCH Verlag GmbH & Co. KgaA), particularly Chapter 1; Kaczorowski, et al. (2011) *Frontiers in Pharmacology*, 2(78): 1-11; Cardoso, et al. (2015)*Mol Pharmacol*, 88(2): 291-303; Felix, et al. (2004) *Assay Drug Dev Technol*, 2: 260-268; and Deuis, et al., (2016) *Toxins*, 8(3): 78.

EXAMPLES

Certain embodiments of the invention will now be described with reference to the following examples, which are intended for the purpose of illustration only and are not intended to limit the scope of the generality hereinbefore described.

All materials and reagents used in the synthesis and testing of the peptides are commercially available, for example, from Sigma-Aldrich Co. (Castle Hill, NSW, Australia) unless otherwise stated. Amino acids and resins are available from, for example, Protein Technologies, Inc. (Tucson, USA), Sigma-Aldrich Co. and the Peptide Institute, Inc. (Osaka, Japan).

Data were plotted and analysed using Prism (GraphPad Software, La Jolla, Calif., USA), version 6.0. Statistical significance was defined as P<0.05 and was determined by t-test or one-way ANOVA with Dunnett's post test. Data is expressed as the mean±standard error of the mean (SEM).
Animals For behavioural assessment adult male C57BL/6J mice aged 6-8 weeks were used. Animals were housed in groups of 3 or 4 per cage, under 12 h light-dark cycles and had standard rodent chow and water ad libitum.

Ethical approval for in vivo experiments in animals was obtained from The University of Queensland animal ethics committee. Experiments involving animals were conducted in accordance with the Animal Care and Protection Regulation Qld (2012), the *Australian Code of Practice for the Care and Use of Animals for Scientific Purposes*, 8th edition (2013) and the *International Association for the Study of Pain Guidelines for the Use of Animals in Research*.

Example 1 Isolation of Pnc1a from *Pamphobeteus Nigricolor* Venom

Figure 1:
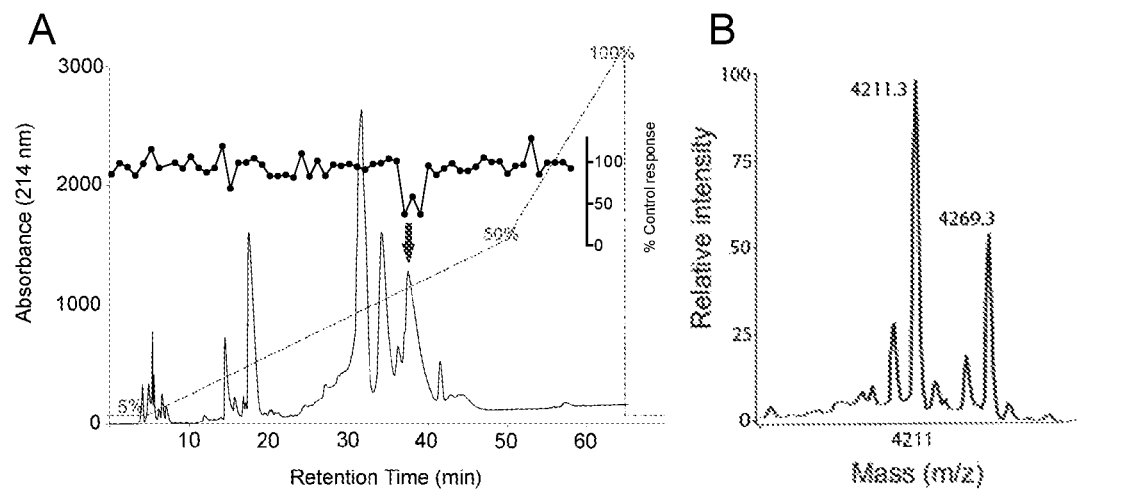
FIG. 1 Isolation of Pnc1a from the venom of *Pamphobeteus nigricolor*. (A) Crude venom isolated from *Pamphobeteus nigricolor* (1 mg) was fractionated on a Vydac 218TP C18 column with a two-step linear acetonitrile/0.1% formic acid gradient (5-50% B/45 min, 50-100% B/15 min; dashed line). The corresponding activity of each 1 min fraction on Na$_v$1.3 responses in HEK 293 cells is shown above (black circles). The fractions containing Pnc1a (arrow; elution at 38% B) partially inhibited veratridine-induced Na$_v$1.3 responses. (B) Native peptide purified by RP-HPLC was analysed on a MALDI-TOF mass spectrometer. MALDI-TOF-MS revealed two dominant masses present; (M+H), 4211.3 m/z and 4269.3 m/z. (C) Edman degradation identified two novel 35 residue sequences, differing only by the N-terminal amino acid, consistent with the two observed masses (M+H).

Crude venom was isolated from a single specimen of *P. nigricolor* by applying a mild electrical current to the chelicerae to stimulate venom secretion. Crude venom was dissolved in 5% acetonitrile/0.1% formic acid, vortexed and centrifuged at 12,000 g for 5 min to remove insoluble material. Crude venom (1 mg) was fractionated using reversed-phase high-performance liquid chromatography (RP-HPLC) on a UltiMate 3000 (Dionex, Sunnyvale, Calif., USA) into 60×1 min fractions with a Vydac 218TP C18 column (250×4.6 mm, 5 µm) using the following gradient: 5% solvent B for 5 minutes, followed by 5-50% solvent B over 45 min followed by 50-100% solvent B over 15 minutes, at a flow rate of 0.7 mL/min (solvent A, $H_2O$/0.1% formic acid; solvent B, 90% acetonitrile/0.1% formic acid) (FIG. 1A). Crude venom fractions (0.2% equivalent of 1 mg crude venom) were freeze-dried and re-constituted in 15 µL physiological salt solution (PSS; composition in mM: NaCl 140, glucose 11.5, KCl 5.9, $MgCl_2$ 1.4, $NaH_2PO_4$ 1.2, $NaHCO_3$ 5, $CaCl_2$ 1.8, 2-[4-(2-hydroxyethyl)piperazin-1-yl] ethanesulfonic acid (HEPES) 10; pH 7.4) for activity testing using a Fluorescent Imaging Plate Reader (FLIPR) membrane potential assay at $Na_v1.3$.

HEK293 cells stably expressing $rNa_v1.3$ (obtained from Prof. Stephen Waxman, Yale School of Medicine, USA) were cultured in Dulbecco's modified eagle medium (DMEM) containing 10% v/v foetal bovine serum (FBS) and G-418 (0.5 mg/mL). Cells were grown in a humidified 5% $CO_2$ incubator at 37° C., grown to 70-80% confluence, and passaged every 3-4 days using TrypLE Express (Invitrogen).

Activity-guided fractionation of *P. nigricolor* venom was carried out in HEK 293 cells stably expressing $rNa_v1.3$. Cells were plated 48 h before the assay on 384-well black walled imaging plates at a density of 10,000 to 15,000 cells per well and were loaded with red membrane potential dye for 30 min at 37° C. (Molecular Devices, CA, USA). One vial of bulk red membrane potential dye was reconstituted to a 10 x stock solution with PSS and stored at −20° C. and diluted to 1× solution with PSS on the day of the assay. After addition of fractionated *P. nigricolor* venom diluted in 0.1% BSA using the $FLIPR^{TETRA}$, cells were incubated a further 5 min before stimulating $Na_v$ using veratridine (60 µM). Changes in membrane potential were assessed using the $FLIPR^{TETRA}$ (excitation 515 to 545 nm, emission 565 to 625 nm) every second for 300 s after adding agonists.

Active fractions were analysed on a MALDI-TOF mass spectrometer (4700 Proteomics Analyzer, Applied Biosystems, Mulgrave, VIC) using α-cyano-4-hydroxycinnamic acid (CHCA) 7 mg/mL as the matrix in 50% acetonitrile mixed 1:1 (v/v) and re-fractionated to near-purity on a Ascentis Express Peptide ES-C18 column (150×2.1 mm, 2.7 µm) using the following gradient: 5% solvent B for 5 minutes, followed by 5-25% solvent B over 5 min followed by 25-55% solvent B over 50 minutes, followed by 55-100% solvent B over 5 minutes at a flow rate of 0.3 mL/min (solvent A, $H_2O$/0.1% formic acid; solvent B, 90% acetonitrile/0.1% formic acid). Near-pure fractions (0.2% equivalent of 1 mg crude venom) were freeze-dried and re-constituted in 15 µL PSS and activity was confirmed using a FLIPR membrane potential assay at $Na_v1.3$ as described above. Active fractions were re-analysed by MALDI-TOF. Two dominant masses were identified in the active fractions (i.e. fractions that partially inhibited veratridine-induced $Na_v1.3$ responses) corresponding to 4211.3 m/z and 4269.3 m/z (M+H) (FIG. 1B). Near-pure venom (0.3% equivalent of 1 mg crude venom) was freeze-dried and sent to the Australian Proteome Research Facility (Macquarie University, NSW, Australia) for Edman degradation.

Edman degradation identified two novel 35 residue sequences differing only by the N-terminal amino acid, consistent with the two observed masses above (FIG. 1C). The sequences were designated Pnc1a and Pnc1b and are shown in SEQ ID NO: 7 and 8, respectively.

Example 2 Synthesis of Pnc1a and Analogues

Solvents for reversed-phase HPLC consisted of 0.05% TFA/$H_2O$ (A) and 90% MeCN/0.043% TFA/$H_2O$ (B). Analytical RP-HPLC was performed on a Shimadzu LC20AT system using a Thermo Hypersil GOLD 2.1×100 mm C18 column heated at 40° C. with flow rate of 0.3 mL/min. A gradient of 10 to 55% B over 30 min was used, with detection at 214 nm. Preparative RP-HPLC was performed on a Vydac 218TP1022 column running at a flow rate of 16 mL/min using a gradient of 5 to 45% B over 40 min. Mass spectrometry was performed on an API2000 (ABI Sciex) mass spectrometer in positive ion mode.

Pnc1a and analogues were assembled on a Symphony (Protein Technologies Inc.) automated peptide synthesiser on H-Thr(tBu)-2-ClTrt (for C-terminal carboxylates, loading 0.67 mmol/g) or Fmoc-Rink amide (for C-terminal carboxamides, loading 0.62 mmol/g) polystyrene resin on a 0.1 mmol scale. Fmoc deprotections were achieved using 30% piperidine/N,N-dimethylformamide (DMF) (1×1.5 min, then 1×4 min). Couplings were performed in DMF using 5 equivalents of Fmoc-amino acid/2-(1H-benzotriazol-1-yl)-1,1,3,3-tetramethyluronium hexafluorophosphate (HBTU)/N,N-diisopropylethylamine (DIEA) (1:1:1) relative to resin loading for 2×20 min. Amino acid side-chains were protected as Asp(OtBu), Arg(Pbf), Cys(Trt), Glu (OtBu), His(Trt), Lys(Boc), Thr(tBu), Trp(Boc), Tyr(tBu). N-terminal acetylation was accomplished using acetic anhydride/DIEA (10 equivalents each relative to resin loading) in DMF for 15 min. Cleavage from the resin and removal of side-chain protecting groups was achieved by treatment with 95% trifluoroacetic acid (TFA)/2.5% triisopropylsilane (TIPS)/2.5% $H_2O$ at room temperature for 2 h. After most of the cleavage solution was evaporated under a stream of $N_2$, the product was precipitated and washed with cold $Et_2O$ and lyophilised from 50% acetonitrile/0.1% TFA/$H_2O$ (380 mg crude Pnc1a obtained; ESI-MS (m/z): calc. (avg) 1070.5 $[M+4H]^{4+}$, found 1070.4). The crude product was purified by preparative RP-HPLC.

Purified reduced peptide (20 mg), reduced glutathione (100 equiv) and oxidised glutathione (10 equiv) were dissolved in 8 M urea (20 mL) then added to a solution of 1.35 M urea/5 M $NH_4OAc$ (pH 8.0, 180 mL) and stirred at 4° C. with exposure to air for 48 h. The single major product was isolated by preparative RP-HPLC.

All further experimentation was performed using synthetic Pnc1a or Pnc1a analogues.

Example 3 $Na_v$ Subtype Selectivity of Pnc1a Assessed Using Membrane Potential Assays HEK293 cells stably expressing $hNa_v1.1$, $hNa_v1.2$, $hNa_v1.3$, $hNa_v1.4$, $hNa_v1.5$, $hNa_v1.6$, $hNa_v1.7$ and $hNa_v1.8$ (SB Drug Discovery, Glasgow, UK) were cultured in minimum essential media (MEM) containing 10% v/v FBS supplemented with L-glutamine (2 mM) and selection antibiotics G-418 (0.5 mg/mL), blasticidin (2-4 µg/mL) and zeocin (0.5 mg/mL) as recommended by the manufacturer. CHO cells stably expressing $hNa_v1.8$ in a tetracycline-inducible system (Chantest, OH, USA) were cultured in Ham's F-12 containing 10% v/v FBS and selection antibiotics as recommended by the manufacturer. To induce $hNa_v1.8$ expression, cells were cultured in the presence of tetracycline (1 µg/mL) for 24 h at 27° C. Cells were grown in a humidified 5% $CO_2$ incubator at 37° C., grown to 70-80% confluence, and passaged every 3-4 days using TryPLE Express (Invitrogen).

Activity of synthetic Pnc1a (Example 2) was assessed in HEK 293 cells stably expressing $hNa_v1.1$-1.8. Cells were plated 48 h before the assay on 384-well black walled imaging plates at a density of 10,000 to 15,000 cells per well and were loaded with red membrane potential dye for 30 min at 37° C. (Molecular Devices, CA, USA). One vial of bulk red membrane potential dye was reconstituted to a 10× stock solution with PSS and stored at −20° C. and diluted to 1× solution with PSS on the day of the assay. After addition of synthetic Pnc1a (Example 2) diluted in 0.1% BSA using the FLIPR$^{TETRA}$, cells were incubated a further 5 min before stimulating $Na_v$ using veratridine (60 µM, $Na_v1.1$-$Na_v1.7$; Alomone) or deltamethrin (150 µM, $Na_v1.8$; Sigma-Aldrich Co.). Changes in membrane potential were assessed using the FLIPR$^{TETRA}$ (excitation 515 to 545 nm, emission 565 to 625 nm) every second for 300 s after adding agonists.

Figure 2:
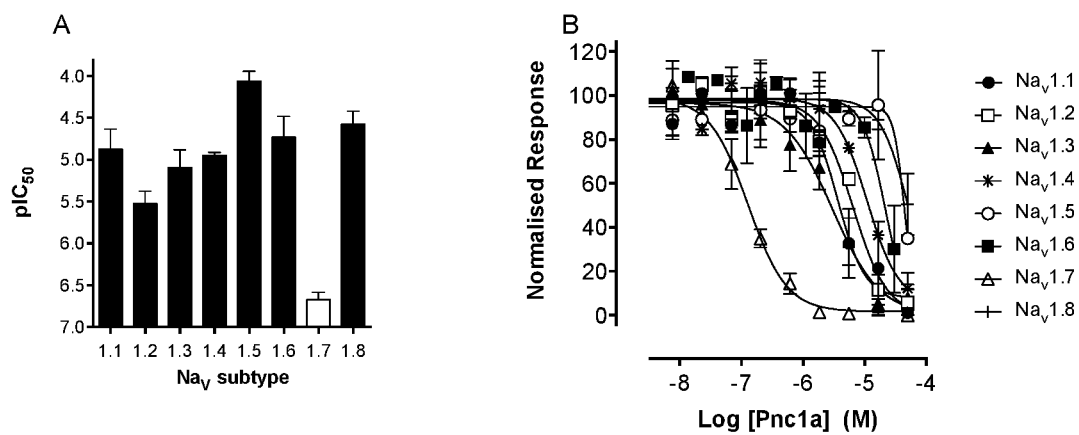
FIG. 2 Na$_v$ subtype selectivity of Pnc1a assessed using membrane potential assays. Activity of synthetic Pnc1a was assessed in HEK cells heterologously expressing hNa$_v$1.1-

Pnc1a most potently inhibited $Na_v1.7$ ($pIC_{50}$ 6.67±0.09 M) with greater than 10 fold selectivity over $Na_v1.2$ ($pIC_{50}$ 5.53±0.1 M), $Na_v1.3$ ($pIC_{50}$ 5.09±0.2 M), greater than 50 fold selectivity over $Na_v1.4$ ($pIC_{50}$ 4.95±0.04 M), $Na_v1.1$ ($pIC_{50}$ 4.88±0.2 M) and $Na_v1.6$ ($pIC_{50}$ 4.73±0.2 M), and greater than 100 fold selectivity over $Na_v1.8$ ($pIC_{50}$ 4.58±0.2 M) and the major off target $Na_v1.5$ ($pIC_{50}$ 4.07±0.1 M) (FIGS. 2A and 2B).

Example 4 $Na_v$ Subtype Selectivity of Pnc1a and Activity of [K24D]Pnc1a at $Na_v1.7$ Assessed Using Automated Patch Clamping HEK293 cells stably expressing $hNa_v1.1$-1.7 or CHO cells stably expressing $hNa_v1.8$ (as described in Example 3 above) were cultured in a T-175 flask in selection antibiotic-free media at 37° C. Cells were grown to 70-80% confluence and harvested using Detachin (Bio-Scientific, NSW, Australia) at 37° C. for 2 min. Dissociated cells were then resuspended in Ex-Cell ACF CHO Medium with HEPES (25 mM; Sigma-Aldrich Co.) and allowed to recover on the QStirrer for 30 min.

The extracellular solution contained in mM: NaCl 145, KCl 4, $CaCl_2$ 2, $MgCl_2$ 1, HEPES 10 and glucose 10. The pH was adjusted to 7.4 with NaOH and osmolarity was adjusted with sucrose to 305 mOsm. The intracellular solution contained in mM: CsF 140, ethylene glycol tetraacetic acid (EGTA)/CsOH 1/5, HEPES 10 and NaCl 10. The pH was adjusted to 7.3 with CsOH and osmolarity adjusted with sucrose to 320 mOsm. Synthetic Pnc1a (Example 2) or [K24D]Pnc1a (SEQ ID NO: 21; prepared according to the procedure of Example 2) were diluted in extracellular solution with 0.1% bovine serum albumin (BSA).

[SEQ ID NO: 21]
DCRYMFGDCEKDEDCCKHLGCKRDMKYCAWDFTFT

Whole-cell patch-clamp experiments were performed on a QPatch-16 automated electrophysiology platform (Sophion Bioscience, Ballerup, Denmark) using 16-channel planar patch chip plates (QPlates; Sophion Bioscience) with a patch hole diameter of 1 µm and resistance of 2±0.02 MΩ with the following parameters: positioning pressure −60 mbar, minimum seal resistance 0.1 GΩ, holding potential −100 mV, holding pressure −20 mbar.

Whole-cell currents were filtered at 5 kHz and acquired at 25 kHz.

To determine the concentration-response of Pnc1a at $Na_v1.1$-1.8, a 20 ms depolarisation to −20 mV (+10 mV for $Na_v1.8$) was applied at 0.05 Hz from a holding potential of −80 mV and a 100 ms pre-pulse to −120 mV. The current-voltage (IV) curve was constructed with a holding potential of −80 mV followed by a pre-pulse of −100 mV for 50 ms and a series of 50 ms step pulses that ranged from −80 to 50 mV in 5 mV increments before returning to a holding potential of −80 mV. Voltage-dependence of activation was determined as normalized $Na_v$ conductance ($G_{Na}$) using: $G_{Na}=I_{Na}/(V_{memb}-V_{rev})$, where $V_{memb}$ is the membrane potential and $V_{rev}$ is the reversal potential for each cell. The voltage of activation data was fitted to a Boltzmann sigmoidal curve using GraphPad Prism, version 6.0.

Electrophysiology at $Na_v1.9$ was performed in HEK293 cells expressing $hNa_v1.9$ using the Molecular Devices PatchXpress automated patch clamp platform.

Cells were seeded at $2 \times 10^6$ cells per T-75 flask for 2 days in culture. At the time of the experiment the cell count was $6\text{-}10 \times 10^6$ cells per flask. Cells were washed (1×) in Dulbecco's phosphate buffered saline (DPBS; Hyclone) for a short 30 second swirl. 1 mL of 1× 0.05% Trypsin-ethylenediaminetetraacetic acid (EDTA) (Gibco) was added and swirled around to cover the bottom of the flask and was allowed to sit on the cells for about 4 mins. 10 mL of warmed media (DMEM high glucose media, Hyclone, supplemented with 10% FBS, 2 mM sodium pyruvate, 10 mM HEPES and 400 µg/mL G-418) was added to inactivate trypsin. Cells were triturated until a single cell suspension was achieved. Cells were aliquoted into 250 mL centrifuge tubes at a concentration of $2 \times 10^5$ cells/mL. The 250 mL centrifuge tube was placed on a rocker in an incubator set at 28° C. and was gently rocked for approximately 1 hr to allow cells to recover. Cell aliquots of 5 mL ($1 \times 10^6$ cells) were placed in a 15 mL centrifuge tube and spun at 100×g for 2 minutes. The supernatant was removed leaving a cell pellet. 100 µL of external recording solution was added to the pellet and triturated 20 times to get a single cell suspension, which was then placed in a 1.5 mL tube for placement in the PatchXpress.

The extracellular solution contained in mM: NaCl 135, KCl 5.4, $CaCl_2$ 2, $MgCl_2$ 1, HEPES 10 and glucose 5. The pH was adjusted to 7.4 with NaOH and osmolarity was adjusted with sucrose to 300 mOsm. The intracellular solution contained in mM: CsF 135, EGTA/CsCl 10/5, HEPES 10 and NaCl 5. The pH was adjusted to 7.4 with CsOH and osmolarity adjusted with sucrose to 298 mOsm. Synthetic Pnc1a (Example 2) was diluted in extracellular solution with 0.1% BSA.

Cells were voltage clamped at −140 mV and 40 ms depolarizing voltage steps to −40 mV applied at a frequency of 0.05 Hz until current amplitude was steady (automatically determined by PatchXpress scripts), at which time the solution in the well(s) containing clamped cell(s) was exchanged with 45 µL of a solution comprising Pnc1a. Another exchange of 45 µL Pnc1a solution was repeated approximately 11 s later.

Pnc1a most potently inhibited $Na_v1.7$ ($pIC_{50} > 9.04 \pm 0.4$ M), with greater than 30-fold selectivity over $Na_v1.1$ ($pIC_{50}$ 7.43±0.1 M), greater than 100-fold selectivity over $Na_v1.2$ ($pIC_{50}$ 6.90±0.1 M), $Na_v1.3$ ($pIC_{50}$ 6.68±0.1 M), $Na_v1.4$ ($pIC_{50}$ 6.80±0.1 M) and $Na_v1.6$ ($pIC_{50}$ 6.89±0.1 M), and greater than 1000 fold selectivity over $Na_v1.5$ ($pIC_{50}$ 6.01±0.1 M), $Na_v1.8$ ($pIC_{50}$ 4.32±0.1 M) and $Na_v1.9$ ($pIC_{50}$ 5.63±0.1 M) (FIGS. 3A and 3B).

At $hNa_v1.7$, Pnc1a shifted the voltage dependence of activation to a more depolarised potential ($V_{50}$; Control, −25.1±0.5 mV; Pnc1a (100 nM), −3.82±0.8 mV; Pnc1a (10 nM), −4.40±2.2 mV; Pnc1a (0.3 nM), −28.94±0.66 mV) (FIGS. 4A and 4B). Pnc1a (100 nM) had no effect on the voltage dependence of slow inactivation (FIG. 4C) or fast inactivation (FIG. 4D). The analogue [K24D]Pnc1a (100 nM) had minimal effect on the current voltage (IV) relationship of $Na_v1.7$, demonstrating the importance of lysine 24 for activity (FIG. 5).

Example 5 Effect of Pnc1a on Pain Behaviours in the OD1 Model

OD1 was diluted in phosphate-buffered saline/0.1% BSA (300 nM) and administered by shallow subcutaneous (intraplantar) injection to the left hind paw of mice in a volume of 40 µL under light isoflurane (3%) anesthesia. Mice were then placed individually into polyvinyl boxes (10×10×10 cm), and spontaneous pain behavior (licks and flinches) was counted by an investigator unaware of the treatments received from video recordings for 10 min post-injection. Synthetic Pnc1a (Example 2) or ProTxII (Peptides International) delivered by the intraplantar route was co-injected with OD1 at the concentrations stated. Synthetic Pnc1a (Example 2) delivered by the intraperitoneal route was administered 15 min prior to injection of OD1 at the doses stated in a volume of 10 µL/g.

Intraplantar administration of Pnc1a (100 nM, 300 nM, 1 µM) and intraperitoneal administration of Pnc1a (0.3, 1, 3 mg/kg) concentration-dependently reversed spontaneous pain behaviours in mice evoked by OD1 (FIGS. 6A and 6B, and FIG. 7). Intraplantar administration of the $Na_v1.7$ selective inhibitor ProTxII (1 µM) only partially reversed OD1-induced pain behaviours compared to an equivalent concentration of Pnc1a (FIG. 6C).

Example 6 Motor Assessment of Systemically Delivered Pnc1a Compared to Other $Na_v1.7$ Clinical Candidates and the Adjuvant Analgesic Gabapentin Motor performance was assessed using the Parallel Rod Floor Test and analyzed using ANY-Maze software (Stoelting Co., version 4.70, Wood Dale, Ill., USA). Synthetic Pnc1a (3 mg/kg) (Example 2), GpTx-1 (0.1 mg/kg; synthesised in accordance with the protocol of Example 2), PF-04856264 (30 mg/kg; Sigma-Aldrich Co.) and CNV1014802 (30 mg/kg; Axon MedChem) were administered by the intraperitoneal route 15 min prior to assessment of motor performance. Mice were then placed in the Parallel Rod Floor Test apparatus, and the distance travelled (m) and number of foot slips were recorded over 1 min using the ANY-Maze software. The ataxia index was calculated by dividing the number of foot slips by the distance travelled (m).

Pnc1a (3 mg/kg), PF-04856254 (30 mg/kg) and CNV1014802 (30 mg/kg) had no significant effect compared to vehicle control, whereas the spider peptide GpTx-1 (0.1 mg/kg) and gabapentin (100 mg/kg) caused a significant increase in the ataxia index (FIG. 8).

Example 7 Effect of Pnc1a on Burns-Induced Pain

To induce a mild burn injury, the plantar skin of the left hind paw of mice was applied with firm pressure to a Peltier plate (Hot/Cold Plate, Ugo Basile, Comerio, Italy) set at 52.5° C. for 25 s under light isoflurane (3%) anaesthesia. Behavioural assessment (mechanical and thermal thresholds) was performed 3 days after the burns injury. Synthetic Pnc1a (Example 2) was delivered by the intraplantar route 10 min prior to behavioural assessment.

Intraplantar administration of Pnc1a had no significant effect on the mechanical threshold (FIG. 9A) but significantly increased the thermal threshold of the injured paw (FIG. 9B).

Example 8 Effect of Pnc1a on Ciguatoxin-Induced Spontaneous Pain

Ciguatoxin (P-CTX-1; isolated in accordance with the protocol of Hamilton et al. (2002) *Toxicon*, 40(6): 685-693) was diluted in phosphate-buffered saline/0.1% BSA (10 nM) and administered by shallow subcutaneous (intraplantar) injection to the left hind paw of mice in a volume of 40 µL under light isoflurane (3%) anesthesia. Mice were then placed individually into polyvinyl boxes (10×10×10 cm), and spontaneous pain behavior (licks and flinches) was counted by an investigator unaware of the treatments received from video recordings for 10 min post-injection. Synthetic Pnc1a (Example 2) delivered by the intraplantar route was co-injected with ciguatoxin at the concentrations stated.

Intraplantar administration of Pnc1a significantly reduced spontaneous pain behaviours (FIG. 10).

Example 9 Effect of Pnc1a in Combination with the Opioid, Oxycodone, in Pain Models λ-Carrageenan (Sigma-Aldrich Co.) was dissolved in phosphate buffered saline to a 1% w/v solution (prepared 24 h prior) and administered by intraplantar injection to the left hind paw of mice in a volume of 40 µL under light isoflurane (3%) anaesthesia. Behavioural assessment (mechanical and thermal thresholds) was performed 3 hours after injection of carrageenan. Test compounds, including synthetic Pnc1a (Example 2), oxycodone (Mundipharma Pty Ltd) and naloxone methiodide (Sigma-Aldrich Co.), delivered by the intraperitoneal route were administered 10 min prior to behavioural assessment at the doses stated in a volume of 10 µL/g.

Mechanical allodynia was assessed using an electronic von Frey apparatus (MouseMet Electronic von Frey, TopCat Metrology Ltd, United Kingdom). Mice were habituated in individual mouse runs for at least 5 min prior to testing. A soft-tipped 0.3 mm diameter flat-ended polypropylene probe was applied to the plantar surface of each hind paw with pressured applied at a force rise rate of ~1 g/s. The force that elicited paw withdrawal was calculated using the MouseMet Software. The paw withdrawal force (PWF) was determined from the average of three tests, separated by at least 2 min.

Mice were habituated in individual mouse runs for at least 5 min prior to testing. The test utilises a novel automated thermal probe device (MouseMet Thermal, Topcat Metrology Ltd, United Kingdom) consisting of a 2.5 mm diameter, slightly rounded, lead-free solder/brass probe that is mounted on the measurement arm of a MouseMet electronic von Frey transducer. Heating of the probe is triggered when the device handle is rotated while the probe is lightly placed against the plantar surface of the mouse paw. The resultant force (~1 g) depresses the measurement arm and initiates heating of the probe while in contact with the mouse's paw, ensuring consistent thermal transfer. The probe is preheated to ~37° C. before coming in contact with the paw, then once in contact heats at a rate of 2.5° C./sec, with a cut out set at 60° C. to prevent tissue damage. Removal of the paw and/or the probe by the investigator terminates heating, and triggers display of the withdrawal temperature on the readout, without the need for the investigator to manually stop the heating or record the temperature, until the reset button is pressed. The temperature that elicited a paw withdrawal, known as the paw withdrawal temperature (PWT), was determined by a single test.

The combination of Pnc1a (3 mg/kg) and oxycodone (0.3 mg/kg) significantly alleviated mechanical allodynia compared to vehicle control and oxycodone alone. The analgesic effects of the combination were reversed by the peripherally restricted opioid antagonist naloxone methiodide (100 mg/kg) (FIG. 11A). The combination of Pnc1a (3 mg/kg) and oxycodone (1 mg/kg) significantly alleviated thermal allodynia compared to vehicle control and oxycodone alone. The analgesic effects of the combination were reversed by the peripherally restricted opioid antagonist naloxone methiodide (100 mg/kg) (FIG. 11B).

Formalin (formaldehyde 16% w/v, Thermo Scientific, Australia) was diluted in saline to a 1% w/v formaldehyde solution and was administered by shallow subcutaneous (intraplantar) injection to the left hind paw of mice in a volume of 20 µL under light isoflurane anaesthesia. Mice were then placed individually into polyvinyl boxes (10×10× 10 cm), and spontaneous pain behavior (licks and flinches) was counted by an investigator unaware of the treatments received from video recordings for 50 min in 5 min intervals post-injection. Phase I and Phase II were defined as the cumulative pain behaviours that occurred from 0-10 min and 10-45 min postinjection, respectively. Test compounds delivered by the intraperitoneal route were administered at the same time as formalin at the doses stated in a volume of 10 µL/g.

The combination of Pnc1a (3 mg/kg) and oxycodone (1 mg/kg) significantly reduced spontanous pain behaviours compared to vehicle control in Phase I and II. The effect resulting from the combination of Pnc1a and oxycodone was also greater than either agent alone (FIGS. 12A and 12B).

Example 10 $Na_v$ Subtype Selectivity of Pnc1a Analogues Assessed Using Membrane Potential Assays Synthetic Pnc1a and Pnc1a analogues detailed in Table 4 were synthesised according to the protocol of Example 2.

TABLE 4

Pnc1a analogues

| Analogue name | SEQ ID NO | Modification from Pnc1a | Sequence |
|---|---|---|---|
| Ac-Pnc1a | — | N-terminal acetylation | Ac-DCRYMFGDCEKDEDCCKHLGCKRKMKYCAWDFTFT-OH |
| S0-Pnc1a | 9 | Addition of Serine to the N-terminus | SDCRYMFGDCEKDEDCCKHLGCKRKMKYCAWDFTFT-OH |
| [M5,25Nle]Pnc1a | 10 | Mutation of Met 5 and Met 25 to Nle | DCRYX$_2$FGDCEKDEDCCKHLGCKRKX$_8$KYCAWDFTFT-OH Wherein X$_2$ and X$_8$ = Nle |
| [R23K]Pnc1a | 11 | Mutation of Arg 23 to Lys | DCRYMFGDCEKDEDCCKHLGCKKKMKYCAWDFTFT-OH |

TABLE 4-continued

Pnc1a analogues

| Analogue name | SEQ ID NO | Modification from Pnc1a | Sequence |
|---|---|---|---|
| Pnc1a-CONH$_2$ | — | C-terminal amidation | DCRYMFGDCEKDEDCCKHLGCKRKMKYCAWDFTFT-NH$_2$ |
| [D8G]Pnc1a | 12 | Mutation of Asp 8 to Gly | DCRYMFGGCEKDEDCCKHLGCKRKMKYCAWDFTFT-OH |
| [E13A]Pnc1a | 13 | Mutation of Glu 13 to Ala | DCRYMFGDCEKDADCCKHLGCKRKMKYCAWDFTFT-OH |

The activity of Pnc1a and the Pnc1a analogues was assessed in HEK 293 cells stably expressing hNa$_v$1.1-1.8 using the protocol described in Example 3.

All Pnc1a analogues retained the ability to inhibit Na$_v$1.7, with [D8G]Pnc1a being the most potent Na$_v$1.7 inhibitor (IC$_{50}$=0.049 µM) (Table 5 and FIG. 13). The selectivity over other Na$_v$ subtypes varied between the analogues, with Ac-Pnc1a being the most selective over Na$_v$1.1, [R23K] Pnc1a being the most selective over Na$_v$1.2, S0-Pnc1a being the most selective over Na$_v$1.3 and Na$_v$1.6, and [D8G]Pnc1a being the most selective over Na$_v$1.4, Na$_v$1.5 and Na$_v$1.8.

TABLE 5

Na$_v$ subtype selectivity of Pnc1a analogues assessed using membrane potential assay

| Analogue name | Na$_v$ subtype | IC$_{50}$ (µM) | Selectivity for Na$_v$1.7 |
|---|---|---|---|
| Ac-Pnc1a | 1.1 | 23 | 41 |
|  | 1.2 | 5 | 8 |
|  | 1.3 | 8 | 13 |
|  | 1.4 | 14 | 24 |
|  | 1.5 | >30 | >53 |
|  | 1.6 | 16 | 29 |
|  | 1.7 | 0.572 | 1 |
|  | 1.8 | >30 | >53 |
| S0-Pnc1a | 1.1 | 9 | 32 |
|  | 1.2 | 3 | 10 |
|  | 1.3 | 6 | 22 |
|  | 1.4 | 11 | 40 |
|  | 1.5 | >30 | >107 |
|  | 1.6 | 19 | 68 |
|  | 1.7 | 0.282 | 1 |
|  | 1.8 | >30 | >107 |
| [M5,25Nle]Pnc1a | 1.1 | 2 | 17 |
|  | 1.2 | 0.773 | 7 |
|  | 1.3 | 1 | 10 |
|  | 1.4 | 3 | 22 |
|  | 1.5 | >30 | >260 |
|  | 1.6 | 5 | 41 |
|  | 1.7 | 0.116 | 1 |
|  | 1.8 | >30 | >260 |
| [R23K]Pnc1a | 1.1 | 8 | 33 |
|  | 1.2 | 3 | 14 |
|  | 1.3 | 5 | 19 |
|  | 1.4 | 10 | 40 |
|  | 1.5 | >30 | >120 |
|  | 1.6 | 16 | 63 |
|  | 1.7 | 0.251 | 1 |
|  | 1.8 | >30 | >120 |
| Pnc1a-CONH$_2$ | 1.1 | 8 | 18 |
|  | 1.2 | 3 | 7 |
|  | 1.3 | 7 | 15 |
|  | 1.4 | 16 | 35 |
|  | 1.5 | >30 | >65 |
|  | 1.6 | 20 | 44 |
|  | 1.7 | 0.461 | 1 |
|  | 1.8 | >30 | >65 |
| [D8G]Pnc1a | 1.1 | 2 | 35 |
|  | 1.2 | 0.301 | 6 |
|  | 1.3 | 0.658 | 13 |
|  | 1.4 | 2 | 48 |
|  | 1.5 | >30 | >616 |
|  | 1.6 | 2 | 46 |
|  | 1.7 | 0.049 | 1 |
|  | 1.8 | >30 | >616 |
| [E13A]Pnc1a | 1.1 | 4 | 29 |
|  | 1.2 | 0.566 | 4 |
|  | 1.3 | 2 | 18 |
|  | 1.4 | 5 | 36 |
|  | 1.5 | >30 | >217 |
|  | 1.6 | 8 | 61 |
|  | 1.7 | 0.139 | 1 |
|  | 1.8 | >30 | >217 |

Example 11 Na$_v$ Subtype Selectivity of Pnc1a Analogues Assessed Using Membrane Potential Assays Synthetic Pnc1a analogues detailed in Table 6 were synthesised according to the protocol of Example 2.

TABLE 6

Pnc1a analogues

| Analogue name | SEQ ID NO | Modification from Pnc1a | Sequence |
|---|---|---|---|
| [D8K]Pnc1a | 14 | Mutation of Asp 8 to Lys | DCRYMFGKCEKDEDCCKHLGCKRKMKYCAWDFTFT-OH |
| [D8N]Pnc1a | 15 | Mutation of Asp 8 to Asn | DCRYMFGNCEKDEDCCKHLGCKRKMKYCAWDFTFT-OH |
| [D1K]Pnc1a | 16 | Mutation of Asp 1 to Lys | KCRYMFGDCEKDEDCCKHLGCKRKMKYCAWDFTFT-OH |

TABLE 6-continued

Pnc1a analogues

| Analogue name | SEQ ID NO | Modification from Pnc1a | Sequence |
|---|---|---|---|
| [K24R]Pnc1a | 17 | Mutation of Lys 24 to Arg | DCRYMFGDCEKDEDCCKHLGCKRRMKYCAWDFTFT-OH |
| [K24D]Pnc1a | 21 | Mutation of Lys 24 to Asp | DCRYMFGDCEKDEDCCKHLGCKRDMKYCAWDFTFT-OH |
| [W30A]Pnc1a | 22 | Mutation of Trp 30 to Ala | DCRYMFGDCEKDEDCCKHLGCKRKMKYCAADFTFT-OH |
| [Y4A]Pnc1a | 18 | Mutation of Tyr 4 to Ala | DCRAMFGDCEKDEDCCKHLGCKRKMKYCAWDFTFT-OH |
| [E10K]Pnc1a | 19 | Mutation to Glu 10 to Lys | DCRYMFGDCKKDEDCCKHLGCKRKMKYCAWDFTFT-OH |
| [E13K]Pnc1a | 20 | Mutation of Glu 13 to Lys | DCRYMFGDCEKDKDCCKHLGCKRKMKYCAWDFTFT-OH |

The activity of the Pnc1a analogues was assessed in HEK 293 cells stably expressing hNa$_v$1.1-1.8 using the protocol described in Example 3.

Interestingly, substitution of Lys 24 with Asp resulted in only partial inhibition of Na$_v$1.7, indicating that a basic residue at position 24 is important for Na$_v$1.7 inhibition (Table 7). All other analogues retained the ability to inhibit Na$_v$1.7. However, substitution of Trp 30 with Ala resulted in a decrease in potency and selectivity, with this peptide having greatest potency at Na$_v$1.5. [D8K]Pnc1a was the most potent inhibitor of Na$_v$1.7 and also had the greatest selectivity over Na$_v$1.5.

TABLE 7

Na$_v$ subtype selectivity of Pnc1a analogues assessed using membrane potential assay

| Analogue name | Na$_v$ subtype | IC$_{50}$ (µM) | Selectivity for Na$_v$1.7 |
|---|---|---|---|
| [D8K]Pnc1a | 1.1 | 0.241 | 19 |
| | 1.2 | 0.040 | 3 |
| | 1.3 | 2 | 159 |
| | 1.4 | 0.663 | 52 |
| | 1.5 | >30 | >2000 |
| | 1.6 | >30 | >2000 |
| | 1.7 | 0.013 | 1 |
| | 1.8 | >30 | >2000 |
| [D8N]Pnc1a | 1.1 | 0.349 | 14 |
| | 1.2 | 0.147 | 6 |
| | 1.3 | 3 | 118 |
| | 1.4 | 0.852 | 35 |
| | 1.5 | >30 | >1000 |
| | 1.6 | >30 | >1000 |
| | 1.7 | 0.024 | 1 |
| | 1.8 | >30 | >1000 |
| [D1K]Pnc1a | 1.1 | 0.754 | 24 |
| | 1.2 | 0.261 | 8 |
| | 1.3 | 4 | 134 |
| | 1.4 | 3 | 86 |
| | 1.5 | >30 | >900 |
| | 1.6 | >30 | >900 |
| | 1.7 | 0.031 | 1 |
| | 1.8 | >30 | >900 |
| [K24R]Pnc1a | 1.1 | 0.856 | 27 |
| | 1.2 | 0.414 | 13 |
| | 1.3 | 8 | 260 |
| | 1.4 | 3 | 102 |
| | 1.5 | >30 | >900 |
| | 1.6 | >30 | >900 |
| | 1.7 | 0.031 | 1 |
| | 1.8 | >30 | >900 |
| [K24D]Pnc1a | 1.1 | 32 | 63 |
| | 1.2 | 38 | 7 |
| | 1.3 | 20 | 39 |
| | 1.4 | 12 | 24 |
| | 1.5 | >30 | 59 |
| | 1.6 | >30 | 14 |
| | 1.7 | 0.510* | 1 |
| | 1.8 | >30 | 40 |
| [W30A]Pnc1a | 1.1 | 15 | 2 |
| | 1.2 | 24 | 3 |
| | 1.3 | 11 | 2 |
| | 1.4 | 12 | 2 |
| | 1.5 | 6 | 0.9 |
| | 1.6 | >30 | 4 |
| | 1.7 | 7 | 1 |
| | 1.8 | >30 | 4 |
| [Y4A]Pnc1a | 1.1 | 17 | 19 |
| | 1.2 | 8 | 8 |
| | 1.3 | 20 | 22 |
| | 1.4 | 12 | 12 |
| | 1.5 | 18 | 20 |
| | 1.6 | >30 | >30 |
| | 1.7 | 0.934 | 1 |
| | 1.8 | >30 | >30 |
| [E10K]Pnc1a | 1.1 | 0.384 | 9 |
| | 1.2 | 0.172 | 4 |
| | 1.3 | 5 | 128 |
| | 1.4 | 2 | 49 |
| | 1.5 | 13 | 326 |
| | 1.6 | 0.820 | 20 |
| | 1.7 | 0.041 | 1 |
| | 1.8 | >30 | >700 |
| [E13K]Pnc1a | 1.1 | 0.830 | 9 |
| | 1.2 | 0.378 | 4 |
| | 1.3 | 6 | 66 |
| | 1.4 | 2 | 27 |
| | 1.5 | >30 | >300 |
| | 1.6 | 1 | 14 |
| | 1.7 | 0.97 | 1 |
| | 1.8 | >30 | >300 | where * indicates partial inhibition.

Example 12 Effect of Pnc1a on Post-Operative Pain

To induce post-operative (post-surgical) pain, the plantar skin of the hind paw of mice was incised under light isoflurane (3%) anaesthesia. Briefly, a 7 mm longitudinal incision was made through the skin and fascia 3 mm from the proximal edge of the heel using a sterile surgical scalpel (#11). The underlying plantaris muscle was elevated and also incised longitudinally. The wound was closed with two silk sutures. Mechanical allodynia was assessed 24 h after the incisional injury. Synthetic Pnc1a (Example 2) or a vehicle control were delivered by the intraplantar route (3 µM) and intraperitoneal route (3 mg/kg) 10 min prior to behavioural assessment.

Pnc1a significantly increased the mechanical threshold of the injured paw compared to vehicle alone when administered via both the intraplantar (P<0.05) and intraperitoneal (P<0.05) routes (FIGS. 14A and 14B).

Example 13 Activity of Pnc1a at hERG Assessed Using Automated Patch Clamping

CHO cells stably expressing hERG (B'SYS GmbH, Witterswil, Switzerland) were cultured in Ham's F-12 medium containing 10% v/v FBS and selection antibiotics as recommended by the manufacturer. Cells were cultured and prepared as described in Example 4.

The extracellular solution contained in mM: NaCl 145, KCl 4, $MgCl_2$ 1, $CaCl_2$ 2, HEPES 10 and glucose 10. The pH was adjusted to 7.4 and osmolarity was 305 mOsm. The intracellular solution contained in mM; KCl 120, HEPES 10, $CaCl_2$ 5, $MgCl_2$ 1.7, $K_2ATP$ 4, EGTA 10.

The pH was adjusted to 7.3 and osmolarity was 292 mOsm. Synthetic Pnc1a (Example 2) was diluted in extracellular solution with 0.1% bovine serum albumin (BSA).

Whole-cell patch-clamp experiments were performed on a QPatch-16 automated electrophysiology platform (as described in Example 4). hERG currents were elicited by a depolarization step of +40 mV from a holding potential of −80 mV for 5 s. hERG tail currents were elicited upon partial repolarization to −50 mV for 5 s. The interval of voltages pulses was 15 s.

hERG potassium channels are essential for normal electrical activity in the heart, with inhibition of these channels causing long QT syndrome. Pnc1a (100 nM) did not have a significant effect on hERG peak tail current (FIG. 15; control, 539±13 pA; Pnc1a, 504±38 pA).

Example 14 Stability of Pnc1a

The stability of synthetic Pnc1a (Example 2) was assessed in saline (pH 3), phosphate buffered saline (PBS; pH 6.5), PBS/saline (pH 5.7), and bicarbonate buffered saline ($HCO_3^-$/saline; pH 5.7 and pH 7.1). Pnc1a (100 µM) was incubated in the above solutions at room temperature (approximately 22° C.) for a period of 25 days. The amount of Pnc1a was quantified using RP-HPLC/MS and subsequent integration of the relevant peak size.

Pnc1a remained intact over the 25 day period in saline at pH 3 and bicarbonate buffered saline at both pH 5.7 and 7.1 (FIG. 16). Pnc1a had lower stability in PBS at pH 6.5 and PBS/saline at pH 5.7, with no intact peptide remaining after 12 and 25 days, respectively (FIG. 16).

The disclosure of every patent, patent application, and publication cited herein is hereby incorporated herein by reference in its entirety.

The claims defining the invention are as follows:

1. An isolated, synthetic or recombinant peptide comprising, consisting or consisting essentially of SEQ ID NO: 1:

[SEQ ID NO: 1]
CRXaa$_1$Xaa$_2$FGXaa$_3$CXaa$_4$KDXaa$_5$DCCKHLGCKXaa$_6$Xaa$_7$Xaa$_8$KYC wherein:
Xaa$_1$ is selected from aromatic amino acid residues including Phe, Tyr and Trp, and small amino acid residues including Ser, Thr, Ala and Gly;
Xaa$_2$ and Xaa$_8$ are independently selected from hydrophobic amino acid residues including Met, Nle, Ile, Leu and Val;
Xaa$_3$ is selected from charged amino acid residues including Glu, Asp, Lys and Arg, small amino acid residues including Ser, Thr, Ala and Gly, and large, polar amino acid residues including Asn and Gln;
Xaa$_4$ is selected from charged amino acid residues including Glu, Asp, Lys and Arg;
Xaa$_5$ is selected from charged amino acid residues including Glu, Asp, Lys and Arg, and small amino acid residues including Ser, Thr, Ala and Gly; and
Xaa$_6$ and Xaa$_7$ are independently selected from basic amino acid residues including Arg and Lys.

2. The peptide according to claim 1, wherein Xaa$_1$ is Tyr or Ala.

3. The peptide according to claim 1, wherein Xaa$_2$ is Nle.

4. The peptide according to claim 1, wherein Xaa$_3$ is Asp, Gly, Lys or Asn.

5. The peptide according to claim 1, wherein Xaa$_4$ is Glu or Lys.

6. The peptide according to claim 1, wherein Xaa$_5$ is Ala, Glu or Lys.

7. The peptide according to claim 1, wherein Xaa$_8$ is Nle.

8. The peptide according to claim 1, wherein the peptide comprises, consists or consists essentially of:

[SEQ ID NO: 7]
DCRYMFGDCEKDEDCCKHLGCKRKMKYCAWDFTFT;

[SEQ ID NO: 8]
GCRYMFGDCEKDEDCCKHLGCKRKMKYCAWDFTFT;

[SEQ ID NO: 9]
SDCRYMFGDCEKDEDCCKHLGCKRKMKYCAWDFTFT;

[SEQ ID NO: 10]
DCRYXaa$_2$FGDCEKDEDCCKHLGCKRKXaa$_8$KYCAWDFTFT;

[SEQ ID NO: 11]
DCRYMFGDCEKDEDCCKHLGCKKKMKYCAWDFTFT;

[SEQ ID NO: 12]
DCRYMFGGCEKDEDCCKHLGCKRKMKYCAWDFTFT;

[SEQ ID NO: 13]
DCRYMFGDCEKDADCCKHLGCKRKMKYCAWDFTFT;

[SEQ ID NO: 14]
DCRYMFGKCEKDEDCCKHLGCKRKMKYCAWDFTFT;

[SEQ ID NO: 15]
DCRYMFGNCEKDEDCCKHLGCKRKMKYCAWDFTFT;

[SEQ ID NO: 16]
KCRYMFGDCEKDEDCCKHLGCKRKMKYCAWDFTFT;

[SEQ ID NO: 17]
DCRYMFGDCEKDEDCCKHLGCKRRMKYCAWDFTFT;

```
                                                       [SEQ ID NO: 18]
DCRAMFGDCEKDEDCCKHLGCKRKMKYCAWDFTFT;

[SEQ ID NO: 19]
DCRYMFGDCKKDEDCCKHLGCKRKMKYCAWDFTFT;
or

[SEQ ID NO: 20]
DCRYMFGDCEKDKDCCKHLGCKRKMKYCAWDFTFT;
``` wherein $Xaa_2$ and $Xaa_8$ are Nle.

9. An isolated, synthetic or recombinant peptide comprising, consisting or consisting essentially of SEQ ID NO: 4:

```
                                                        [SEQ ID NO: 4]
CRYXaa2FGXaa3CEKDXaa5DCCKHLGCKXaa6KXaa8KYC
``` wherein:

$Xaa_2$ and $Xaa_8$ are independently selected from hydrophobic amino acid residues including Met, Nle, Be, Leu and Val;

$Xaa_3$ and $Xaa_5$ are independently selected from acidic amino acid residues including Glu and Asp, and small amino acid residues including Ser, Thr, Ala and Gly; and $Xaa_6$ is selected from basic amino acid residues including Arg and Lys.

10. The peptide according to claim 9, wherein the peptide comprises, consists or consists essentially of the amino acid sequence of SEQ ID NO: 7:

```
                                                        [SEQ ID NO: 7]
DCRYMFGDCEKDEDCCKHLGCKRKMKYCAWDFTFT.
```

11. The peptide according to claim 1, wherein the cysteine residues are bonded in pairs to form three disulfide bonds.

12. The peptide according to claim 11, wherein the disulfide bonds are formed between the side chains of Cys I and Cys IV, Cys II and Cys V, and Cys III and Cys VI (numbered from the N-terminus).

13. A composition comprising a peptide according to claim 1 and a pharmaceutically acceptable carrier or diluent.

14. A method of inhibiting $Na_v1.7$, comprising contacting a $Na_v1.7$ expressing cell with the peptide according to claim 1.

15. A method of treating or preventing a condition in respect of which inhibition of $Na_v1.7$ activity is associated with effective treatment, comprising administration of the peptide according to claim 1.

16. The method according to claim 15, wherein the condition is pain itch or cough.

17. The method according to claim 16, wherein the pain is selected from neuropathic, inflammatory and nociceptive pain.

18. The method according to claim 15, wherein the condition is selected from inherited erythromelalgia, paroxysmal extreme pain disorder and peripheral neuropathy.

19. The method of claim 17, further comprising administration of an agent that has analgesic activity.

20. The method of claim 19, wherein the agent that has analgesic activity is an opioid analgesic.

* * * * *